(12) United States Patent
Bar et al.

(10) Patent No.: US 6,696,454 B2
(45) Date of Patent: Feb. 24, 2004

(54) INHIBITORS OF SPERMIDINE SYNTHASE FOR THE TREATMENT OF OSTEOARTHRITIS AND CARTILAGE REHABILITATION

(75) Inventors: Dganit Bar, Rehovot (IL); Elena Feinstein, Rehovot (IL); Orit Segev, Rehovot (IL)

(73) Assignees: Quark Biotech, Inc., Cleveland, OH (US); Shionogi & Co., Ltd., Osaka (JP)

( * ) Notice: Subject to any disclaimer, the term of this patent is extended or adjusted under 35 U.S.C. 154(b) by 0 days.

(21) Appl. No.: 10/023,038

(22) Filed: Dec. 12, 2001

(65) Prior Publication Data

US 2002/0160978 A1 Oct. 31, 2002

Related U.S. Application Data

(60) Provisional application No. 60/254,850, filed on Dec. 12, 2000.

(51) Int. Cl.$^7$ ............................................... B32B 17/03
(52) U.S. Cl. ....................................................... 514/262
(58) Field of Search .............................. 514/262, 266, 514/663

(56) References Cited

U.S. PATENT DOCUMENTS 5,514,703 A    5/1996    Carlson et al.

OTHER PUBLICATIONS

Nakashim, Kunio; "Synthesis of N–chlorosulfonyl Dicyclohexylamine as a Potent Inhibitor oFor Spermidine Synthase and Its Effects on Human Leukemia MOLT4B Cells"; 1986; Biochemical and Biophysical Research Communications; vol. 141, pp. 718–722.*

Pegg et al. Effects of S–andenosyl–1, 8–diamino–3–thioctane on Polyamine Metabolism. Biochem. 1982; 21(20): 5082–5089.

Shirahata et al. Effects of Inhibitors of Spermindine Synthase and Spermine Synthase on Polyamine Synthesis in Rat Tissues. Biochem. Pharmacol. 1993; 45(9): 1897–1903.

Slotkin et al.. Polyamides in brain and Heart of the Neonatal Rat: Effects of Inhibitors of Ornithine Decarboxylase and Spermidine Synthase. Life Sci. 1984; 35(10):1125–1131.

Trentham et al. Autoimmunity to Type II Collagen: An Experimental Model of Arthritis. J. Exp. Med. 1977; 146: 857–868 et al. CAPRI regulates $Ca^{+2}$–dependent inactivation of the Ras–MAPK pathway. Current Biology. 2001; 11:981–986.

Kong et al. Activated T cells regulate bone loss and joint destruction in adjuvant arthritis through steoprotegerin ligand. Biochem. Nature. Nov. 18, 1999; 402: 304–309.

Han et al. Effects of Sodium Hyaluronate on Experimental Osteoarthritis in Rabbit Knee Joints. Nayoga J. Med. Sci. 1999; 62(3–4): 115–126.

Cohen et al. Storing live embryonic and adult human cartilage grafts for transplantation using a joint simulating device. Biomaterials. 2000; 21: 2117–2123.

Vittur et al. A possible role for polyamines in cartilage in the mechanism of calcification. Biochem Biophys Acta. Mar. 19, 1986; 881(1): 38–45.

Nesher et al. Effect of treatment with methotrexate, hydroxychloroquine, and prednisone on lymphocyte polyamine levels in rheumatoid arhritis: Correlation with the clinical response and rheumatoid factor synthesis. Clin. Exp. Rheumatol. Jul.–Aug. 1997; 15(4): 343–347.

Wolos et al. Mathylacetylenic Putrescine (MAP), an Inhibitor of Polyamine Biosynthesis, Prevents the Development of Collagen–Induced Arthritis. Cell Immunol. Feb. 1990; 125(2): 498–507.

Lakanen et al., Synthesis and Biochemical Evaluation of Adenosylspermidine, a Nucleoside–Polyamine Adduct Inhibitor of Spermidine Synthase. J. Med. Chem. 38:2714–2727 (1995).

Liu and Coward, Stereospecific Synthesis of (R)– and (S)–S–Adenosyl–1,8–diamino–3–thioctane, a Potent Inhibiotr of Polyamine Biosynthesis. Comparison of Asymmetric Induction vs. Enantiomeric Synthesis. J. Med. Chem. 34:2094–2101 (1991).

* cited by examiner

Primary Examiner—Theodore J. Criares
(74) Attorney, Agent, or Firm—John P. White; Cooper & Dunham LLP

(57) ABSTRACT

This invention provides a method for the treatment of a subject in need of treatment for osteoarthritis comprising administering to said subject an amount of an inhibitor of spermidine biosynthesis sufficient to effect a substantial inhibition of spermidine biosynthesis. This invention also provides the use of an inhibitor of spermidine biosynthesis in the treatment of a subject in need of treatment of osteoarthritis in an amount sufficient to effect a substantial inhibition of spermidine biosynthesis. This invention further provides a method of preparing a therapeutic composition for the treatment of a subject in need of a treatment for osteoarthritis and the invention further provides a method of identifying an inhibitor of spermidine biosynthesis, whereby the inhibitor is a spermidine synthase inhibitor.

3 Claims, 5 Drawing Sheets

1  2  3  4  5  6  7

35kDa

INHIBITORS OF SPERMIDINE SYNTHASE FOR THE TREATMENT OF OSTEOARTHRITIS AND CARTILAGE REHABILITATION

This invention is a continuation-in-part and claims the benefit of U.S. Provisional Application No. 60/254,850, filed Dec. 12, 2000, the contents of which are hereby incorporated by reference into this application.

FIELD OF THE INVENTION

The invention relates to the involvement of spermidine synthase with the development of osteoarthritis and in cartilage rehabilitation. More particularly, the invention relates to methods of treatment, compositions and the use of spermidine synthase inhibitors in the treatment of osteoarthritis and cartilage damage associated therewith.

BACKGROUND OF THE INVENTION

Osteoarthritis (OA) is a common, debilitating, costly, and currently incurable disease. Novel approaches to therapy are clearly required. The disease is characterized by abnormal functioning of chondrocytes, their terminal differentiation and initiation of osteogenesis within articular cartilage tissue, and breakdown of normal cartilage matrix. Genes whose products are involved in chondrogenesis and osteogenesis starting from the common progenitor cells, genes determining the terminal differentiation of chondrocytes and genes whose products trigger breakdown of the cartilaginous matrix are obvious candidates for therapeutic intervention.
Epidemiology of OA OA, also erroneously called degenerative joint disease, represents failure of a diarthrodial (movable, synovial-lined) joint. In idiopathic (primary) OA, the most common form of the disease, no predisposing factor is apparent.

Secondary OA is pathologically indistinguishable from idiopathic OA but is attributable to an underlying cause. OA is the most common of all human joint disorders and is the most prevalent arthritic condition in the United States and around the world. Estimates of OA prevalence based on clinical evaluation in various studies show that more than 90% of the population over the age of 70 has OA. The invention is aimed at novel avenues of therapy and prevention of the disease.
Pathogenesis of OA OA is a heterogeneous group of conditions that lead to joint symptoms and signs associated with defective integrity of articular cartilage, in addition to related changes in the underlying bone at the joint margins. OA may be either idiopathic (i.e., primary) or secondary to other medical conditions (inflammatory, biochemical, endocrine-related, metabolic, and anatomic or developmental abnormalities). Age is the most powerful risk factor for OA but major trauma and repetitive joint use are also important risk factors for OA. The pattern of joint involvement in OA is also influenced by prior vocational or avocational overload.

The disease has two general stages: (1) compensated and (2) decompensated. Currently, most investigators feel that the primary changes occur in cartilage extracellular matrix due to exogenous reasons (i.e., load, injury etc.). Then, a defect in the collagen network of the cartilage is apparent, and lysosomal enzymes and secreted proteases (MMPs, plasmin, cathepsins) probably account for the observed initial alterations in cartilage matrix. Their synthesis and secretion are stimulated by IL-1 or by other factors (e.g., mechanical stimuli). In the initial stage of disease, compensatory cellular response is activated. Secreted by chondrocytes, protease inhibitors like TIMP and PAI-1 work to stabilize the system by opposing the protease activity. Growth factors such as IGF-1 and TGF-$\beta$ are implicated in repair processes that may heal the lesion or, at least, stabilize the process by activating proliferation of cells of chondrogenic lineage. Finally, this leads to the accumulation of hypertrophic chondrocytes. The latter cells have marked biosynthetic activity that is expressed in increasing the proteoglycan (PG) concentration, associated with thickening of the cartilage ("compensated" OA). The compensatory mechanisms may maintain the joint in a reasonably functional state for years. However, the repair tissue does not hold up and the rate of PG synthesis falls off with full-thickness loss of cartilage. This marks the decompensated stage of OA. Following the destruction of the articular cartilage, there is migration of progenitor cells to the sites of tissue damage. These cells proliferate and differentiate into four cell types: osteoblasts, chondroblasts, chondroclasts and fibroblasts, which combine to form bony structures called osteophytes which protrude into the joint space, thus inhibiting its movement. Finally, gradual replacement of cartilage with bone occurs.

The reason for this phenomenon is unknown. One possibility is that in OA, the normal inhibitory growth control of articular chondrocytes or synovial membrane fibroblasts is altered. This enables accumulation of two types of cells that cannot be found in normal articular cartilage: (1) immature mesenchymal and bone marrow cells with modified properties, and (2) hypertrophic articular chondrocytes. Previous results have clearly shown that hypertrophic chondrocytes may trigger osteogenesis by secretion of angiogenic and osteogenic factors. (Homer, A., Bishop, N. J., Bord S., Beeton, C., Kelsall, A. W., Coleman, N. and Compston, J. E. (1999). Immunolocalisation of vascular endothelial growth factor (VEGF) in human neonatal growth plate cartilage. J. Anat. 194: 519–524).

In OA, therapeutic interference may target three main processes:

inhibition of initial cartilage damage—one of the accepted therapeutic strategies, combining recommendations to reduce the physical pressure on the joint and treatment with inhibitors of metalloproteinases;

inhibition or attenuation of total cartilage destruction at later stages—implies the therapeutic activation of processes connected to cartilage rehabilitation, namely, the promotion of proper differentiation of mesenchymal progenitors into mature chondrocytes capable of producing fully functional articular cartilage tissue;

inhibition or attenuation of osteophyte formation at the end stage of the disease—implies the therapeutic inhibition of ectopic osteogenesis at the site of articular cartilage.

Therefore, the inventors set out to identify target genes that code for specific factors that stimulate or inhibit the differentiation of progenitor cells to chondrocytes and/or stimulate or inhibit the differentiation of progenitor cells to osteoblasts.

Changes in gene expression caused by IL-1, FGF-2 and mechanical stress, which are known osteogenic factors, may be connected to OA development and, therefore, should be opposed by therapeutic intervention. Surprisingly, it has been found by the present inventors that one of the genes that were upregulated by FGF-2 is the spermidine synthase gene. This implied that the spermidine synthase gene might be involved in the OA pathway.

Spermidine Synthase

Spermidine is one of three bioactive polyamines, the other two being putrescine and spermine. Polyamines constitute a group of cell components that are important in the regulation of cell proliferation and cell differentiation. Although their exact functions have not yet been clarified, it is assumed that polyamines play an important role in a number of cellular processes such as replication, transcription, and translation.

The polyamine biosynthetic pathway consists of two highly regulated enzymes, ornithine decarboxylase and S-adenosylmethionine decarboxylase, and two constitutively expressed enzymes, spermidine synthase and spermine synthase. Spermidine synthase is a 74 kDa protein that catalyses the 3-aminopropylation of putrescine (1,4-diaminobutane) to produce spermidine. The biosynthesis of spermidine involves decarboxylation of S-adenosylmethionine (SAM) to S-adenosyl-3-methylthiopropanamine (decarboxylated SAM) by SAM decarboxylase, and decarboxylation of ornithine to putrescine by ornithine decarboxylase. Decarboxylated SAM then reacts with spermidine synthase to generate an aminopropylated form of the enzyme, which then transfers the aminopropyl group to putrescine to produce spermidine and 5'-methylthioadenosine (MTA). The active enzyme is a dimer of two identical subunits, requires no cofactors, and uses dcAdoMet as an aminopropyl donor and putrescine as the acceptor.

Putrescine, spermidine and spermine have been found in many living tissues, including cartilage. Their formation, catalyzed by ODC, has been observed during the induction of cartilage transformation in bone. Parathyroid hormone, which stimulates the synthesis of glycosaminoglycans, induces ODC activity and increases polyamine levels in differentiated rabbit costal chondrocytes in culture. Resting cartilage is devoid of putrescine. Ossifying cartilage contains more polyamines than the resting zone (based on tissue weight and DNA content). The amount of spermidine in the ossifying zone is 5-fold higher and that of spermine about 2-fold. The spermidine/spermine ratio is 1.7 in the ossifying cartilage and 0.69 in the resting zone. Only spermidine showed the capacity of displacing proteoglycan subunits from a column of Sepharose 4B-type II collagen (Franco Vittur et al. (1986). A possible role for polyamines in cartilage in the mechanism of calcification. Biochimica et Biophysica Acta 881:38–45).

The effect of polyamines on the interaction of proteoglycan units with collagen was studied by following the elution of proteoglycans from a column of Sepharose 4B-collagen loaded with proteoglycan subunits. While putrescine and spermine were without effect, spermidine showed a strong capacity in displacing proteoglycan subunits: about 90% of the proteoglycan subunits were removed from the column. Spermine and spermidine increased the activity of alkaline phosphatase produced from cartilage. Spermidine was observed in the cells of the resting zone of preosseous cartilage. Cell staining disappeared, approaching the zone of proliferating and columnar cells. Staining for spermidine is markedly evident in the matrix only at the limit of columnar cells where hypertrophy of chondrocytes initiates. Among the three polyamines, spermidine is the most abundant: a high molar ratio of spermidine/spermine has been taken as an index of rapid growth. The highest amount of spermidine is in the ossifying region.

Polyamine Metabolism

The synthesis of the precursors, putrescine and decarboxylated S-adenosylmethionine (dcAdoMet) is brought about by the action of two decarboxylases ornithine decarboxylase (ODC, EC 4.1.1.17) and S-adenosylmethionine decarboxylase (AdoMetDC, SamDC, EC 4.1.1.51). These enzymes are very highly regulated by means of both growth factors and other stimuli that increase their levels, and by polyamines themselves, which reduce their activity. The combined effect of these agents is to adjust the polyamine levels to that needed for cell growth and development. Alternation in the activities of ODC and AdoMetDC are the major forces in controlling polyamine levels. The activities of the aminopropyltransferases, putrescine aminopropyltransferase (PAPT, spermidine synthase, EC 2.5.1.6) and spermidine aminopropyltransferase (SAPT, spermine synthase, EC2.5.1.22) are controlled primarily through the availability of their substrates. In addition to their de novo synthesis within the cells, polyamines can also be obtained as a result of uptake by a specific transport system. This transport system is regulated both negatively by the intracellular polyamine content and positively by growth factors and oncogenes. The presence of the transport system and its enhanced activity as a result of polyamine depletion is a significant factor in ameliorating the effect of the inhibition of polyamine synthesis. The uptake of exogenous polyamines may be a critical factor in the lack of success in clinical trials of these inhibitors as anti-tumor agents. Finally, polyamine levels can be altered as a result of interconversion, oxidation and efflux. The oxidation of polyamines at the terminal nitrogen atoms is accomplished by $Cu^{+2}$-containing oxidases that appear to be located primarily extracellularly, although their complete absence from the cell has not been established. Interconversion and efflux of polyamines from the cell is facilitated by means of the action of spermidine/spermine-N-acetyltransferase (SSAT, EC 2.3.1.57) which acetylates the aminopropyl end of the polyamines forming N-acetylspermine and N-acetylspermidine. These acetyl derivatives bind less tightly to cellular polyanions and are either excreted or rapidly metabolized. They are oxidized at the internal nitrogen atom by a FAD-dependent oxidase called polyamine oxidase (PAO) splitting of N-acetylaminopropanal and converting spermine Into spermidine and spermidine into putrescine. The limiting factor in this pathway is the activity of SSAT, which is normally very low but is induced greatly by an increase in the cellular content of polyamines or by the application of toxic stimuli, which lead to the release of polyamines from membranes and cellular organelles. Under physiological conditions, PAO has little or no activity against non-acetylated polyamines.

It is therefore an object of the invention to identify different spermidine synthase inhibitors and to evaluate their effect as potential drugs for inhibiting or delaying OA.

It is a further object of this invention to provide therapeutic agents for the treatment of OA and for use in cartilage rehabilitation.

These and other objects of the invention will be elaborated on as the description proceeds.

SUMMARY OF THE INVENTION

In a first aspect, the present invention relates to a method for the treatment of a subject in need of treatment for OA, this method comprising administering to said subject an amount of an inhibitor of spermidine biosynthesis sufficient to effect a substantial inhibition of spermidine biosynthesis so as to thereby treat the subject.

In a preferred embodiment the inhibitor administered to said subject is a spermidine synthase inhibitor.

According to a specifically preferred embodiment, the spermidine synthase inhibitor is an inhibitor that leads to inhibition of any one of chondrocyte proliferation, chondrocyte final differentiation, angiogenesis and osteoclastogenesis.

In yet another preferred embodiment the spermidine synthase inhibitor administered to said subject may be selected from the group consisting of adenosyl spermidine, AdoDATO, DCHA, trans-4-methylcyclohexylamine (4MCHA), cyclohexylamine, methylglyoxal bis-(cyclopentylamidinohydrazone) (MGBP), 2-mercaptopropylamine, N-chlorosulfonyldicyclohexylamine, 5'-((3-aminopropyl) ammo)-5'-deoxyadenosine, 1-aminooxyl-3-aminopropane, 5'-(isobutylthio) adenosine, 5'-(methylthio) adenosine and any functional homologs and analogs thereof.

The invention further relates to the use of an inhibitor of one or more steps in the polyamine biosynthetic pathway in the treatment of OA in a mammalian subject. This inhibitor, according to a preferred embodiment, may be an inhibitor of spermidine biosynthesis, and in a more preferred embodiment it may be a spermidine synthase inhibitor and should inhibit the accumulation of spermidine.

According to a specifically preferred embodiment, the spermidine synthase inhibitor used may be an inhibitor that leads to inhibition of any one of chondrocyte proliferation, chondrocyte final differentiation, angiogenesis and osteoclastogenesis.

The spermidine inhibitor used may be selected from known spermidine synthase inhibitors, such as those described hereinabove.

The present invention further provides an inhibitor of the polyamine biosynthetic pathway for use in the treatment of OA in a mammalian subject. This inhibitor may be, according to preferred embodiment, a spermidine synthase inhibitor. More particularly, the inhibitor to be used in the treatment of OA is a spermidine synthase inhibitor that leads to inhibition of chondrocyte proliferation, chondrocyte final differentiation, angiogenesis and osteoclastogenesis.

In yet another aspect, the present invention relates to the use of an inhibitor of the polyamine biosynthetic pathway in the preparation of a pharmaceutical composition for the treatment of OA in a mammalian subject. Preferably, the inhibitor used may be an inhibitor of spermidine biosynthesis, more preferably it may be a spermidine synthase inhibitor; most preferably, this inhibitor is an inhibitor that inhibits the accumulation of spermidine and that leads to inhibition of any one of chondrocyte proliferation, chondrocyte final differentiation, angiogenesis and osteoclastogenesis.

The inhibitor used in the preparation of a pharmaceutical composition for the treatment of OA may be, according to the present invention, selected from the spermidine synthase inhibitors disclosed above.

The present invention further provides a therapeutic composition for the treatment of OA. This composition comprises as an active ingredient an inhibitor of one or more steps in the polyamine biosynthetic pathway. More preferably, the inhibitor is an inhibitor of spermidine biosynthesis. Most preferably, the inhibitor is a spermidine synthase inhibitor.

According to a preferred embodiment, the composition of the invention may optionally further comprise pharmaceutically or veterinarily acceptable carrier, excipient and/or diluent.

Another aspect of the present invention relates to a method of preparing a therapeutic composition for the treatment of OA. This method of preparation comprises the steps of (a) identifying an inhibitor of a spermidine synthase that leads to inhibition of any one of chondrocyte proliferation, chondrocyte final differentiation, angiogenesis and osteoclastogenesis; and (b) admixing said inhibitor with a pharmaceutically acceptable carrier, excipient and/or diluent.

In one preferred embodiment of the present aspect, identification of a spermidine synthase inhibitor suitable for the preparation of a therapeutic composition for the treatment of OA, is performed by the steps of:

(a) obtaining a candidate spermidine synthase inhibitor; and (b) evaluating the effect of said candidate inhibitor on any one of chondrocyte proliferation, chondrocyte final differentiation, angiogenesis and osteoclastogenesis by an evaluating method.

The evaluating method comprises the steps of:

i. providing a test system comprising DNA encoding spermidine synthase;

ii. contacting said system with the said test candidate spermidine synthase inhibitor under conditions which normally lead to expression of spermidine; and iii. determining the effect of the test candidate inhibitor on an end-point indication as compared to a control, wherein said effect is indicative of inhibition of any one of chondrocyte proliferation, chondrocyte final differentiation, angiogenesis and osteoclastogenesis by the test candidate inhibitor.

In a specific embodiment, the test system used by the evaluating method according to the invention may be any one of in vitro cell culture, ex vivo cell culture, ex vivo organ culture and in vivo animal model. In yet another specific embodiment, the spermidine synthase expressed by said test system used in the method of the invention, may be expressed either endogenously or exogenously. This test system may optionally further comprise endogenous and/or exogenous agents that provide suitable conditions for the expression of spermidine and for the detection of an end-point indication for determining any one of chondrocyte proliferation, chondrocyte final differentiation, angiogenesis and osteoclastogenesis.

Depending on the test assay system chosen, inhibition of chondrocyte proliferation, chondrocyte final differentiation, angiogenesis and osteoclastogenesis can be observed in a variety of ways, including intracellular staining assays (including immunohistochemical) and assays affecting an observable parameter; e.g., a physiological readout, such as change in cell cycle.

According to a preferred embodiment, the test system used by the method of the invention for evaluating the effect of said candidate inhibitor is an in vitro transfected cell culture. The cells employed carry an exogenously expressed spermidine synthase.

In an alternative embodiment, the test system used by the method of the invention for evaluation purposes is an ex vivo bone culture, comprising endogenously expressed spermidine synthase. Preferably, the bone culture used is an embryonic bone culture.

Another alternative test system may be an in vivo system, which is an animal model system. According to the method of the invention, use of an animal model for evaluation purposes enables utilizing the development of arthritis as an end-point indication. Where used as an end-point indication, development of arthritis may be determined, for example, by measuring paw thickness of said animal. Any increase in the size of the paw that is less than the increase observed in a control is indicative of inhibition of chondrocyte proliferation, chondrocyte final differentiation, angiogenesis and osteoclastogenesis, or development of arthritis by the test candidate inhibitor.

In one preferred test system, an appropriate animal model may be a transgenic mouse.

In yet another preferred in vivo test system, an arthritic mammalian model expressing endogenous spermidine synthase may be used by the evaluating method of the invention. According to this embodiment, the arthritic animal enables utilizing the development of arthritis as an end-point indication.

According to a particularly preferred embodiment, the arthritic mammal may be an arthritic rat or an arthritic mouse.

A specifically preferred embodiment of the invention relates to method of preparing a therapeutic composition for the treatment of OA. This method comprises the steps of (a) identifying an inhibitor of a spermidine synthase that leads to inhibition of any one of chondrocyte proliferation, chondrocyte final differentiation, angiogenesis and osteoclastogenesis; and (b) admixing said inhibitor with a pharmaceutically acceptable carrier. Identification of a suitable inhibitor involves obtaining a candidate inhibitor and evaluating the effect of the specific candidate. According to this embodiment, a candidate spermidine synthase inhibitor may be obtained for further evaluation, by selecting an inhibitor from the group consisting of adenosyl spermidine, AdoDATO, DCHA, trans-4-methylcyclohexylamine (4MCHA), cyclohexylamine, methylglyoxal bis(cyclopentylamidinohydrazone) (MGBP), 2-mercaptopropylamine, N-chlorosulfonyldicyclohexylamine, 5'-((3-aminopropyl)ammo)-5'-deoxyadenosine, 1-aminooxyl-3-aminopropane, 5'-(isobutylthio) adenosine, 5'-(methylthio) adenosine and any functional homologs and analogs thereof.

Alternatively, a candidate inhibitor may be obtained for further evaluation, by a screening method for a substance that is an inhibitor of spermidine synthase. According to the invention, such screening method comprises the steps of:

(a) providing a mixture comprising spermidine synthase;

(b) contacting said mixture with a test substance under conditions which normally lead to biosynthesis of spermidine; and (c) determining the effect of the test substance on an end-point indication, whereby inhibition of said end point is indicative of inhibition of spermidine synthase by the test substance. According to a specific embodiment of this alternative, the end point indication may be the presence of a product of the spermidine synthase catalytic reaction.

All the above and other characteristics and advantages of the invention will be further understood through the following illustrative and non-limiting description of preferred embodiments thereof, with reference to the appended drawings.

DETAILED DESCRIPTION OF THE INVENTION

Figure 1:
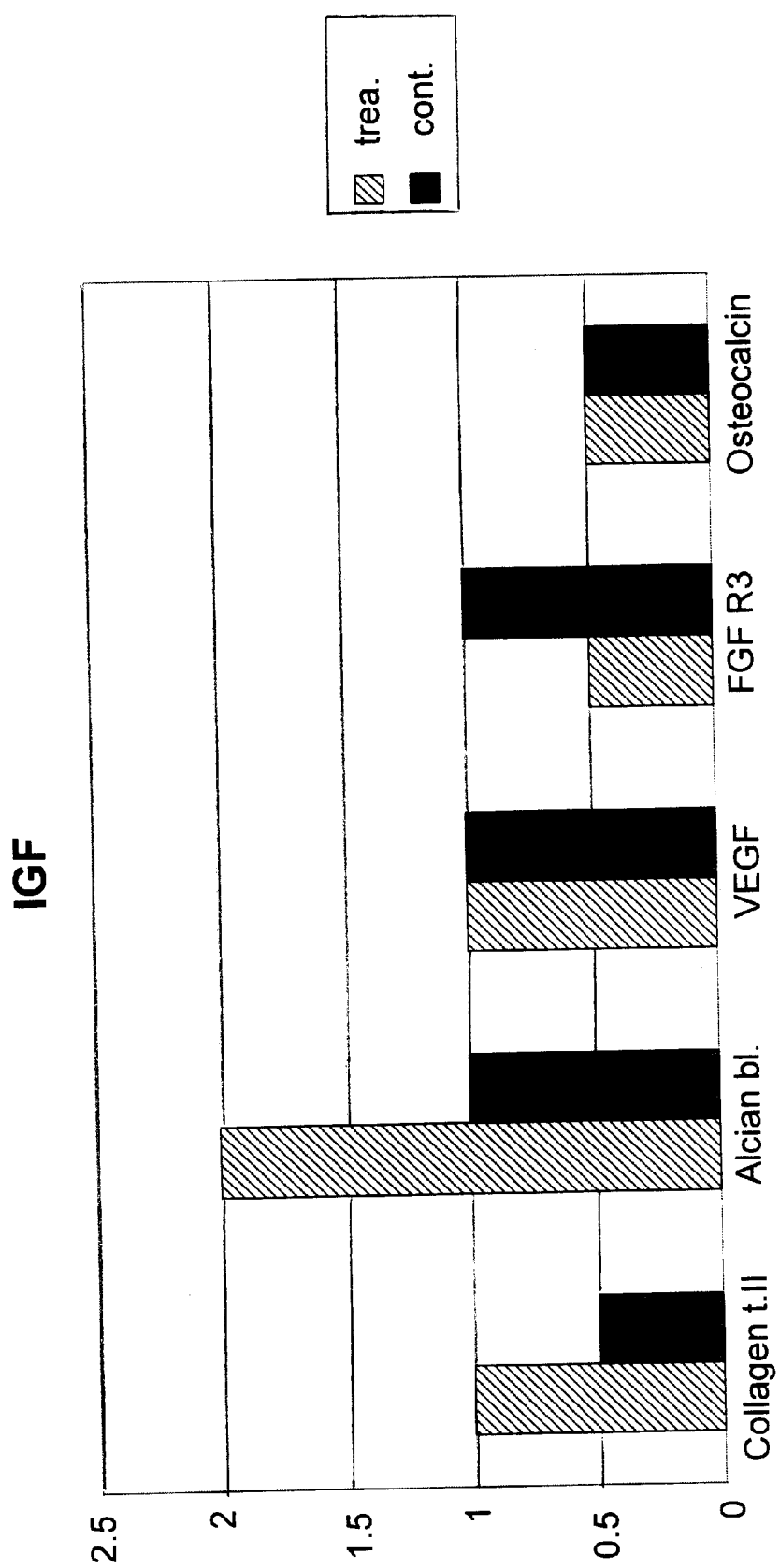
FIG. 1: Expression of various differentiation markers by confluent HMSC cells treated with IGF-1 for 6 days. Control—similarly cultured non-treated cells. The level of marker expression is indicated in relative units. Abbreviations: Cont.=control; trea.=treated; Collagen t. II=Collagen type II; Alcian b1.=Alcian Blue.

The invention will now be further explained through the illustrative and non-limiting description of preferred embodiments.

OA is a destructive joint disease that is characterized not only by degeneration of cartilage but also by ectopic osteogenesis. The inventors employed both an in vitro cell system (HMSC cells) and an ex vivo organ culture (fetal epiphyses grown in a joint simulator) to discover genes that may be important in the development of the disease. The human articular cartilage progenitor cells (HMSC) were used to conduct a series of gene expression profiling experiments. These cells were subjected to various treatments that mimic cartilage rehabilitation (IGF-1) or OA initiation and development (IL1-β, bFGF-2, mechanical stress). In addition to the in vitro studies, ex vivo experiments were also employed, as they better reflect genetic events occurring in the context of complex tissue containing different interacting types of cells. The gene expression profiles corresponding to various applied treatments were studied by microarray hybridization and analyzed by applicant's bioinformatics tools. The gene expression patterns obtained indicated that the chosen in vitro cell system accurately reflects the processes that occur in the OA joint in vivo since many genes known to be markers of OA were identified by the inventors as displaying the expected type of behavior.

The present inventors have identified the spermidine synthase gene, involved in the biosynthesis of spermidine, as a gene that is up-regulated upon bFGF-2 treatment. This finding indicates that the polyamine biosynthetic pathway, particularly the biosynthesis of spermidine and, more specifically, spermidine synthase, is potentially involved in OA, and it thus was selected as a drug target for further development of drugs for the treatment of OA in mammals.

Thus, as a first aspect, the present invention relates to a method for the treatment of a subject in need of treatment for OA, this method comprising administering to said subject an amount of an inhibitor of spermidine biosynthesis effective to inhibit a substantial inhibition of spermidine biosynthesis so as to thereby treat the subject.

By "treatment" is meant the alleviation of the disease state and alleviation of the progression thereof, including the partial or full relief of symptoms associated with the specified disease. "Treatment" may also prevent the disease or delay its onset.

As described in detail in the Background of the Invention, the polyamine biosynthetic pathway involves two highly regulated enzymes, ornithine decarboxylase and S-adenosylmethionine decarboxylase and two constitutively expressed enzymes, spermidine synthase and spermine synthase. The biosynthesis of spermidine involves decarboxylation of S-adenosylmethionine (SAM) to S-adenosyl-3-methylthiopropanamine (decarboxylated SAM) by SAM decarboxylase, and decarboxylation of ornithine to putrescine by ornithine decarboxylase. Decarboxylated SAM then reacts with spermidine synthase to generate an aminopropylated form of the enzyme, which then transfers the aminopropyl group to putrescine to produce spermidine and 5'-methylthioadenosine (MTA). The synthesis of the precursors, putrescine and decarboxylated S-adenosylmethionine (dcAdoMet) is brought about by the action of two decarboxylases, ornithine decarboxylase (ODC, EC 4.1.1.17) and S-adenosylmethionine decarboxylase (AdoMetDC, SamDC. EC 4.1.1.51).

In a preferred embodiment the inhibitor administered to the subject by the method of the invention is a spermidine synthase inhibitor.

The term "inhibitor" as used herein includes homologs and analogs derived from the originally identified inhibiting molecule that retains the polyamine biosynthetic inhibitory activity, more specifically that retains the spermidine biosynthetic inhibitory activity, even more specifically, that retains the specific spermidine synthase inhibitory activity observed in the parent molecule. The term "inhibitor" includes both known inhibitors of the polyamine pathway, specifically, inhibitors of the biosynthesis of spermidine, more specifically inhibitors of spermidine synthase activity, as well as any inhibitors discovered in the screening systems described hereinafter, for example in Example 4.

By the term "substantial inhibition" is meant inhibition of the biosynthesis of spermidine at a level of between 10–90%, more preferably between 25–75%, even more preferably between 40–60%.

According to a specifically preferred embodiment the spermidine synthase inhibitor is an inhibitor that leads to inhibition of any one of chondrocyte proliferation, chondrocyte final differentiation, angiogenesis and osteoclastogenesis.

In yet another preferred embodiment the spermidine synthase inhibitor administered by the method of the invention may be selected from the group consisting of adenosyl spermidine, AdoDATO, DCHA, trans-4-methylcyclohexylamine (4MCHA), cyclohexylamine, methylglyoxal bis(cyclopentylamidinohydrazone) (MGBP), 2-mercaptopropylamine, N-chlorosulfonyldicyclohexylamine, 5'-((3-aminopropyl) amino)-5'-deoxyadenosine, 1-aminooxyl-3-aminopropane, 5'-(isobutylthio) adenosine, 5'-(methylthio) adenosine and any functional homologs and analogs thereof.

Of particular interest amongst the inhibitors listed above are AdoDATO. 4MCHA and DCHA. The literature contains studies that looked at the effects of these inhibitors in cell culture and in vivo. For example AdoDATO, a transition state analog of the transferase reaction, reduced spermidine levels and produced a significant decrease in cell proliferation. Exposure of a variety of mammalian cells to racemic AdoDATO resulted in drastic decrease in cellular spermidine content and a concomitant elevation in putrescine that is consistent with the inhibition of spermidine synthase by the drug (Pegg A E, Tang K C, Coward J K. (1982). Effects of S-adenosyl-1,8-diamino-3-thiooctane on polyamine metabolism. Biochemistry 21(20):5082–5089).

Prolonged exposure of rats to 4MCHA in vivo, for 10 days, led to a 70–80% reduction in spermidine in a variety of tissues, but there was a compensatory increase in spermine such that total polyamine content remained constant, with no obvious effect on growth. Oral administration of 4MCHA for a period of 10 days or 4 months caused a specific and marked decrease in spermidine in rat tissue, with a compensatory increase of spermine (Shirahata A, Takahashi N. Beppu T, Hosoda H. Samejima K. (1993). Effects of inhibitors of spermidine synthase and spermine synthase on polyamine synthesis in rat tissues. Biochem Pharmacol. 45(9):1897–1903).

Daily administration of DCHA to neonatal rats produced a dose-dependent depletion of brain spermidine, accompanied by a rise in putrescine and spermine. Despite continued DCHA treatment, levels of all three polyamines returned to normal within two weeks (Slotkin T A, Bartolome J, Persons D, Whitmore W L. (1984). Polyamines in brain and heart of the neonatal rat: effects of inhibitors of ornithine decarboxylase and spermidine synthase. Life Sci. 35(10):1125–1131).

In a preferred embodiment, the method of the invention is intended for treating a mammalian subject, preferably, a human. Therefore, by "patient", "mammalian subject" or "subject in need" is meant any mammal for which the therapy is desired, including human, bovine, equine, canine, and feline subjects, preferably a human patient.

The therapeutic method of the invention comprises administering an effective amount of said inhibitor to a subject in need. As used herein, "effective amount" means an amount necessary to achieve a selected result. For example, an effective amount of the inhibitor or the composition of the invention is an amount effective for the treatment of the osteoarthritic pathology.

The invention further relates to the use of an inhibitor of one or more steps in the biosynthesis of spermidine in the treatment of OA in a mammalian subject. As in the method of treatment, also in this embodiment the inhibitor according to a preferred embodiment may be a spermidine synthase inhibitor. Preferably, the spermidine synthase inhibitor used in the invention is an inhibitor that leads to inhibition of any one of chondrocyte proliferation, chondrocyte final differentiation, angiogenesis and osteoclastogenesis.

Particularly, the spermidine inhibitor used in the invention may be selected from the group consisting of adenosyl spermidine, AdoDATO, DCHA, trans-4-methylcyclohexylamine (4MCHA), cyclohexylamine, methylglyoxal bis-(cyclopentylamidinohydrazone) (MGMBP), 2-mercaptopropylamine, N-chlorosulfonyldicyclohexylamine, 5'-((3-aminopropyl) amino)-5'-deoxyadenosine, 1-aminooxyl-3-aminopropane, 5-(isobutylthio) adenosine, 5'-(methylthio) adenosine and any functional homologs and analogs thereof.

The present invention further provides an inhibitor of the polyamine biosynthetic pathway for use in the treatment of OA in a mammalian subject. Also in this embodiment the inhibitor is preferably a spermidine synthase inhibitor, more particularly a spermidine synthase inhibitor that leads to inhibition of chondrocyte proliferation, chondrocyte final differentiation, angiogenesis and osteoclastogenesis. Specifically, the spermidine synthase inhibitors provided by the present invention for use in the treatment of OA may be selected from the group consisting of adenosyl spermidine, AdoDATO, DCHA, trans-4-methylcyclohexylamine (4MCHA), cyclohexylamine, methylglyoxal bis-(cyclopentylamidinohydrazone) (MGBP), 2-mercaptopropylamine, N-chlorosulfonyldicyclohexylamine, 5'-((3-aminopropyl) amino)-5'-deoxyadenosine, 1-aminooxyl-3-aminopropane, 5'-(isobutylthio) adenosine, 5'-(methylthio) adenosine and any functional homologs and analogs thereof.

In yet another aspect, the above inhibitors of at least one step of the polyamine biosynthetic pathway, particularly inhibitors of spermidine biosynthesis, and more particularly inhibitors of spermidine synthase, may be used in the preparation of a pharmaceutical composition for the treatment of OA in a mammalian subject.

The present invention further provides a therapeutic composition for the treatment of OA. This composition of the invention comprises as an active ingredient an inhibitor of one or more steps in the polyamine biosynthetic pathway. Preferably, the inhibitor is an inhibitor of spermidine biosynthesis. Most preferably, the inhibitor is a spermidine synthase inhibitor. Particular inhibitors to be comprised in the compositions of the invention are those listed above.

The compositions and methods of the invention are particularly intended for the treatment of OA in humans, but other mammals are also included. These compositions may be administered directly to the subject to be treated or it may be desirable to conjugate them to carrier proteins such as ovalbumin or serum albumin prior to their administration. Therapeutic formulations may be administered in any conventional dosage formulation. Formulations typically comprise at least one active ingredient, as defined above, together with one or more acceptable carriers thereof.

According to a preferred embodiment, the composition of the invention may optionally further comprise a pharmaceutically or veterinarily acceptable carrier, excipient and/or diluent.

Each carrier should be both pharmaceutically and physiologically acceptable in the sense of being compatible with the other ingredients and not injurious to the recipient. While formulations include those suitable for oral, rectal and nasal, preferred formulations are intended for parenteral administration, including intramuscular, intravenous, intradermal and specifically subcutaneous administration. The formulations may conveniently be presented in unit dosage form and may be prepared by any methods known in the art of pharmacy.

The compositions of the invention can be administered in a variety of ways. By way of non-limiting example, the composition may be delivered intravenously, or injected directly into or adjacent to affected joints.

The pharmaceutical forms suitable for injection include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and it must be preserved against the contaminating action of microorganisms, such as bacteria and fungi. The carrier can be solvent or a dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred methods of preparation are vacuum-drying and freeze drying techniques which yield a powder of the active ingredient plus any additional desired ingredient from a previously sterile-filtered solution thereof.

As used herein "pharmaceutically acceptable carrier" includes any and all solvents, dispersion media, coatings, antibacterial and antifungal agents and the like. The use of such media and agents for pharmaceutically active substances is well known in the art. Except as any conventional media or agent is incompatible with the active ingredient, its use in the therapeutic composition is contemplated.

Supplementary active ingredients can also be incorporated into the compositions.

As a preferred route the composition of the present invention may be administered via oral administration, for example, with an inert diluent or with a carrier, or enclosed in a hard or soft shell gelatin capsule, or compressed into tablets, or incorporated directly with the food of the diet.

Composition dosages may be any that ameliorate the symptoms of OA in a patient. It is understood by the skilled artisan that the preferred dosage would be individualized to the patient following good laboratory practices and standard medical practices.

Another aspect of the present invention relates to a method of preparing a therapeutic composition for the treatment of OA. This method comprises the steps of (a) identifying an inhibitor of spermidine synthase that leads to inhibition of any one of chondrocyte proliferation, chondrocyte final differentiation, angiogenesis and osteoclastogenesis; and (b) admixing said inhibitor with a pharmaceutically acceptable carrier.

In one preferred embodiment of the present aspect, identification of a spermidine synthase inhibitor suitable for the preparation of a therapeutic composition for the treatment of OA, is performed by the steps of:

(a) obtaining a candidate spermidine synthase inhibitor; and (b) evaluating the effect of said candidate inhibitor on any one of chondrocyte proliferation, chondrocyte final differentiation, angiogenesis and osteoclastogenesis by an evaluating method.

According to the invention, this evaluating method comprises the steps of:

i. providing a test system comprising DNA encoding spermidine synthase:

ii. contacting said system with the said test candidate spermidine synthase inhibitor under conditions that normally lead to expression of spermidine, and iii. determining the effect of the test candidate inhibitor on an end-point indication as compared to a control, wherein said effect is indicative of inhibition of any one of chondrocyte proliferation, chondrocyte final differentiation, angiogenesis and osteoclastogenesis by the test candidate inhibitor.

Depending on the assay test system chosen, inhibition of chondrocyte proliferation, chondrocyte final differentiation, angiogenesis and osteoclastogenesis can be observed in a variety of ways, including intracellular staining assays (including immunohistochemical) and assays affecting an observable parameter; e.g., a physiological readout, such as change in cell cycle.

In a specific embodiment, the test system used by the evaluating method according to the invention may be any one of in vitro cell culture, ex vivo cell culture, ex vivo organ culture and in vivo animal model.

In yet another specific embodiment, the spermidine synthase expressed by the test system used in the method of the invention, may be expressed either endogenously or exogenously. This test system may optionally further comprise endogenous and/or exogenous agents that provide suitable conditions for the expression of spermidine and for the detection of an end-point indication for determining any one of chondrocyte proliferation, chondrocyte final differentiation, angiogenesis and osteoclastogenesis.

Furthermore, it is to be noted that the effect of the evaluated candidate inhibitor on an end-point indication of the different test systems, may be either elevation or decrease of said end point.

According to a specifically preferred embodiment, the end point indication determined by the method of the invention may be the expression of differentiation markers, which leads to a visually detectable signal. The visually detectable signal may be, but is not limited to, any one of Alcian Blue staining and alizarin red staining. Elevated Alcian Blue staining reflects increased cartilage proteoglycan and is indicative of chondrogenesis, whereas elevated alizarin red staining reflects calcification and is indicative of chondrocyte final differentiation. Therefore, a preferred candidate spermidine synthase inhibitor will be a substance which leads to elevation of Alcian Blue staining and decrease in alizarin red staining.

In another specifically preferred embodiment, the end point indication may be the expression of hypertrophy markers that lead to a visually detectable signal detected by a suitable means. As a non-limiting example, such means for detection of hypertrophy may be immunohistochemical staining for the presence of collagen type X.

Alternatively, the end point indication may be cell proliferation, which may be detected by a suitable means. According to one possibility, cell proliferation may be detected by cell cycle FACS analysis. Alternatively it may be suitable to determine cell proliferation by immunohistochemical staining for the presence of proliferation markers. Preferred proliferation markers may be PCNA.

According to a preferred embodiment, the test system used by the method of the invention for evaluating the effect of said candidate inhibitor is an in vitro transfected cell culture. These cells carry an exogenously expressed spermidine synthase.

In yet another specifically preferred embodiment, the cell or the transfected cell used by the evaluating method of the invention as a test system may be a prokaryotic or eukaryotic cell, particularly a bacterial cell, yeast cell, insect cell, plant cell or preferably a mammalian cell. Most preferred are the RCJ3.IC5.18 cells, a clonal cell population from fetal rat calvaria, which is restricted to the cartilage differentiation pathway (Grigonadis, A. E, Heersche, J N., Aubin, J. E (1996). Analysis of chondroprogenitor frequency and cartilage differentiation in novel family of clonal chondrogenic rat cell line. Differentiation 60:299–307). These cells are stably transfected with pCMVneo expression vector comprising the nucleic acid sequence coding for the spermidine synthase protein.

"Expression Vectors", as used herein, encompass vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and affect expression of the desired genes. These control elements are capable of affecting expression within a suitable host. Generally, the genetic control elements can include a prokaryotic promoter system or a eukaryotic promoter expression control system. Such system typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

The term "operably linked" is used herein for indicating that a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

In general such vectors contain, in addition, specific genes which are capable of providing phenotypic selection in transformed cells. A variety of selectable markers can be incorporated into any construct. For example, a selectable marker which confers a selectable phenotype such as drug resistance, nutritional auxotrophy, resistance to a cytotoxic agent or expression of a surface protein, can be used. The expression vector used by the test system of the invention may further comprise a tag sequence. Such sequences enable the detection and isolation of the recombinant protein. As a non-limiting example such tag sequences may be any one of HA, c-myc, GST, GFP and, preferably, His-6.

The use of prokaryotic and eukaryotic viral expression vectors to express the gene coding for human spermidine synthase according to the present invention, is also contemplated.

The vector is introduced into a host cell by methods known to those of skill in the art. Introduction of the vector into the host cell can be accomplished by any method that introduces the construct into the cell, including, for example, calcium phosphate precipitation, microinjection, electroporation or transformation. See, e.g., Ausubel, F. M. ed. (1989) Current Protocols in Molecular Biology, John Wiley & Sons, New York, incorporated herein by reference.

"Cells" or "transfected cells" are terms used in the present application. It is understood that such terms refer not only to the particular subject cells but also to the progeny or potential progeny of such cells. Because certain modifications may occur in succeeding generations due to either mutation or environmental influences, such progeny may not, in fact, be identical to the parent cell, but are still included within the scope of the term as used herein.

"Transfected cell" as used herein refers to cells that are stably or transiently transfected with vectors constructed using recombinant DNA techniques. A drug resistance or other selectable marker is intended in part to facilitate the selection of the transformants. Additionally, the presence of a selectable marker, such as a drug resistance marker may be of use in keeping contaminating microorganisms from multiplying in the culture medium. Such a pure culture of the transfected cell would be obtained by culturing the cells under conditions that require the induced phenotype for survival.

As used herein, the term "transfection" means the introduction of a nucleic acid, e.g., an expression vector into a recipient cell by nucleic acid-mediated gene transfer.

It is to be appreciated that the cell or the transfected cell used by the in vitro test system of the present invention may further contain an endogenously or exogenously expressible nucleic acid construct encoding possible molecules essential for the biosynthesis of spermidine and for the pathways leading to chondrocyte proliferation, chondrocyte final differentiation, angiogenesis and osteoclastogenesis.

The effect of the candidate spermidine synthase inhibitor on the transfected cell-based test system may be evaluated by examining chondrocyte proliferation using e.g., cell cycle FACS analysis or PCNA, chondrocyte final differentiation by Alcian Blue and alizarin red staining, and chondrocyte hypertrophy using immunohistochemical staining for the presence of collagen type X.

In an alternative embodiment, the test system used by the method of the invention for evaluation purposes is an ex vivo bone culture, comprising an endogenously expressed spermidine synthase. Preferably, the bone culture used may be an embryonic bone culture. Most preferably, said bone culture is a hind leg obtained from a mouse embryo.

The effect of the different candidates on chondrocyte final differentiation will be examined in this test system staining of sections prepared from treated and untreated control bone with Alcian Blue, which stains normal articular cartilage, and alizarin red. Longitudinal growth of bone will be calculated as the increase in length of the hypertrophic region and calcified bone. Hypertrophy will be evaluated in this system using immunohistochemical staining for the presence of collagen type X, and the effect of the candidate inhibitor on chondrocyte proliferation will be determined by PCNA.

Another alternative test system may be an in vivo system, which is an animal model. According to the method of the invention, use of an animal model for evaluation purpose, enables utilizing development of arthritis as an end-point indication. In cases of use as an end point indication, development of arthritis may be determined by measuring paw thickness of the test animal. Any increase of the thickness of the paw less than that of a control is indicative of inhibition of chondrocyte proliferation, chondrocyte final differentiation, angiogenesis and osteoclastogenesis, or development of arthritis by the test candidate inhibitor.

In one preferred test system, an appropriate animal model may be a transgenic mouse expressing exogenous spermidine synthase. More particularly, the transgenic mouse expresses the spermidine synthase gene under the collagen type II promoter.

According to this particular embodiment, evaluation of the effect of a candidate spermidine synthase inhibitor using this in vivo test system, involves applying the test candidate inhibitor to said transgenic mouse under conditions which normally lead to biosynthesis of spermidine. These particular suitable conditions may be, for example, providing a spermidine synthase substrate such as SAM to the tested transgenic mice prior to application of the candidate inhibitor.

As used herein, a "transgenic animal" is any animal, preferably a non-human mammal, possibly also bird or amphibian, in which one or more of the cells of the animal contain the transgene, a heterologous nucleic acid introduced by way of human intervention, such as by transgenic techniques well known in the art. The nucleic acid is introduced into the cell directly or indirectly by introduction into a precursor of the cells by way of deliberate genetic manipulation, such as by microinjection or by infection with a recombinant virus. The term genetic manipulation does not include classical cross-breeding, or in vitro fertilization but, rather, is directed to the introduction of a recombinant DNA molecule. This molecule may be integrated within a chromosome, or it may be extrachromosomally replicating DNA. In the typical transgenic organisms described herein, the transgene causes cells to express a human spermidine synthase gene.

Transgenic animals also include both constitutive and conditional "knock out" animals. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse. The term "transgenic animal" is used herein to refer to animals in which the recombinant gene is found, or in which the recombinant is expressed in some but not all cells of the animal.

As used herein, the term "transgene" means a nucleic acid sequence (encoding e.g., a spermidine synthase), which is partly or entirely heterologous or exogenous, i.e., foreign to the transgenic animal or cell into which it is introduced, or is homologous to an endogenous gene of the transgenic animal or cell into which it is introduced, but which is designed to be inserted, or is inserted, into the animal's genome in such a way as to alter the genome of the cells into which it is inserted, e.g., it is inserted at a location which differs from that of the natural gene, or its insertion results in a knockout or other loss-of-function mutation). A transgene can include one or more transcriptional regulatory sequences and any other nucleic acid, such as introns, that may be necessary for optimal expression of a selected nucleic acid.

It is to be appreciated that, in addition to measuring the development of arthritis, the effect of the candidate inhibitor on the transgenic mouse test system can be also evaluated using the end-point indications as described for the ex vivo test systems disclosed above.

In yet another preferred in vivo test system, an arthritic mammalian model expressing endogenous spermidine synthase may be used by the evaluating method of the invention. According to this embodiment, the arthritic animal enables utilizing the development of arthritis as an end-point indication. Development of arthritis may be determined by measuring the paw thickness of an examined arthritic mammal. Less increase in the size of the paw, as compared to a control, is indicative of inhibition of any one of chondrocyte proliferation, chondrocyte final differentiation, angiogenesis and osteoclastogenesis, and development of arthritis by said test candidate inhibitor. Accordingly, the effect of the candidate inhibitor on the arthritic animal test system will be further examined using the differentiation and proliferation end-points as discussed herein above.

"Animal" for purposes of test animal refers to any animal classified as a mammal suitable for use as an experimental model, such as rats, mice, guinea pigs, hamsters, rabbits, dogs, cats, etc. Preferably, the mammal is any one of a mouse and a rat. It is however to be appreciated that the method and system of the invention may be adapted also for non-mammalian animals.

According to a particularly preferred embodiment, the arthritic mammal may be an arthritic rat or an arthritic mouse that was induced by exogenous means. More particularly, when an arthritic rat is used, a collagen type II-induced arthritis (CIA) female Lewis rat will be preferred A specifically preferred embodiment relates to a method of preparing a therapeutic composition of the invention for the treatment of osteoarthritis (OA). This method comprises the steps of identifying an inhibitor of a spermidine synthase that leads to inhibition of any one of chondrocyte proliferation, chondrocyte final differentiation, angiogenesis and osteoclastogenesis and admixing said inhibitor with a pharmaceutically acceptable carrier. The identification of a suitable inhibitor involves obtaining a candidate inhibitor and evaluating the effect of the specific candidate. According to this specific embodiment, a candidate spermidine synthase inhibitor may be obtained for further evaluation, by selecting an inhibitor from the group consisting of adenosyl spermidine, AdoDATO, DCHA, trans-4-methylcyclohexylamine (4MCHA), cyclohexylamine, methylglyoxal bis-(cyclopentylamidinohydrazone) (MGBP), 2-mercaptopropylamine, N-chlorosulfonyldicyclohexylamine, 5'-((3-aminopropyl) amino)-5'-deoxyadenosine, 1-aminooxyl-3-aminopropane, 5'-(isobutylthio) adenosine, 5'-(methylthio) adenosine and any functional homologs and analogs thereof.

Alternatively, a candidate inhibitor may be obtained for further evaluation by a screening method for a substance that is an inhibitor of spermidine synthase. According to the invention such screening method comprises the steps of:

(a) providing a mixture comprising spermidine synthase;
(b) contacting said mixture with a test substance under conditions that normally lead to biosynthesis of spermidine; and
(c) determining the effect of the test substance on an end-point indication, whereby inhibition of said end point is indicative of inhibition of spermidine synthase by the test substance.

According to a specific embodiment of this alternative, the end point indication may be the presence of a product of the spermidine synthase catalytic reaction. Such product may be any one of spermidine and methyladenosine (MTA). Detection of either of the resulting products may be performed by fluorescent or radioactive labeling, as described in Example 4 hereafter.

The test drug for the screening and evaluation methods of the invention may be any substance selected from the group consisting of protein-based, carbohydrate-based, lipid-based, nucleic acid-based, natural organic-based, synthetically derived organic-based, and antibody-based substances. More specifically, said nucleic acid-based, protein- or antibody-based substance may be a product of a combinatorial library.

As used herein, the term "nucleic acid" refers to polynucleotides such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, double-stranded polynucleotides and single-stranded polynucleotides such as sense or antisense.

Amongst successful candidate drugs or substances will be peptides which mimic regions on the active region of the spermidine synthase, as well as non-peptidic small molecules. Due to their ease of identification, these peptides are particularly useful in alternate forms of the screening assays that detect inhibition of spermidine synthesis. Although the screening assay methods disclosed may not all be suitable for direct screening of large chemical libraries, they do enable sophisticated screening of candidates that can be combined with other techniques for selecting leads.

Disclosed and described, it is to be understood that this invention is not limited to the particular examples, process steps, and materials disclosed herein, as such process steps and materials may vary somewhat. It is also to be understood that the terminology used herein is used for the purpose of describing particular embodiments only and not intended to be limiting since the scope of the present invention will be limited only by the appended claims and equivalents thereof.

It is to be noted that, as used in this specification and the appended claims, the singular forms "a", "an" and "the" include plural referents unless the content clearly dictates otherwise.

Throughout this specification and the claims that follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures
Cell Culture
1. Cell Lines
  1.1. HMSC—Normal adult articular cartilage progenitor cells were obtained from human cartilage. The cartilage was dissected and cultured in fresh DMEM medium supplemented with 10% FCS, L-glutamine and antibiotics. Two weeks after the cultivation of dissected cartilage, the remaining pieces were removed and the attached cells were used.
  1.2. U20S—The human osteoblast-like osteosarcoma cell line was obtained from the American Type Culture Collection (HTB-96).
  1.3. RCJ3.1C5.18—RCJ3.1C5.18 cell line was a gift from Prof. Jane Aubin (University of Toronto, Canada). This cell line is described in: Grigoriadis A. E. Heersche J. N, Aubin J E (1996) Analysis of chondroprogenitor frequency and cartilage differentiation in novel family of clonal chondrogenic rat cell lines. Differentiation, 60:299–307.
  1.4. 293 human kidney cells were obtained from the American Type Culture Collection (CRL-1573).
2. Mechanical Stress HMSC were grown in culture flask to confluence. Secondary subcultures were seeded at the density of $1 \times 10^5$ cell/cm$^2$ onto the flexible polyurethane membranes, which were attached by clamps to a mechanical device. For better cell attachment and growth, the membranes were pretreated with complete serum for 60 minutes at room temperature.

The cells were allowed to adhere to the membranes during 24 hrs. The cultures undergoing a tension (=stretching) treatment were stretched by moving the clamps up to 33%. The tension was kept constant for 1 hour. The cells were collected by mechanical scraping and used for RNA isolation. Compression treatments were performed as follows: The flexible membranes were attached to the mechanical device by clamps and stretched prior to cell seeding by 25% of its original length, then cells were seeded and incubated for adherence for 24 hrs. After 24 hrs, the strain was released and the membranes gained back their original length, forming the compression. This compression was kept for 1 hour prior to RNA extraction, which was performed as described above.

3. Transfection

Stable transfection—RCJ3.1 C5.18 were transfected with the human spermidine synthase gene cloned into the pCM-VNSVneo expression vector using Lipofectamine 2000 reagent (GibcoBRL) according to the manufacturer's instructions. Stable clones were selected after the addition of 0.3 mg G418/ml medium.

RT-PCR

Total RNA was extracted from stable RCJ3.1C5.18 clones using the EZ-RNA isolation kit (Biological Industries) according to the manufacturer's protocol. First strand cDNA synthesis and PCR reaction were performed using the Superscript II kit (GibcoBRL) according to the manufacturer's instructions.

Northern Blot Analysis

Northern blot analysis of human spermidine synthase was performed using RNA extracted from U2OS cells. A blot containing 2 µg of poly(A)+ RNA was probed with the whole ORF of spermidine synthase. Protocol is described in "Current protocols in molecular biology", Ausubel F M et al. (ed), (1987), Vol. 1, Section 4.9.1.

Differentiation Marker Staining

1. Alcian blue—Embryonic bone is fixed with Bouin fixative for 10 minutes, stained with Alcian Blue (1% in 3% acetic acid) for 30 mm and washed with distilled water.

2. Alizarin red—Embryonic bone is fixed in 70% ethanol solution, incubated for 60 minutes on ice and stained with 40 mM alizarin red solution (Sigma) for 10 minutes.

Proliferation Examination

1. PCNA—Immunohistochemistry with anti-PCNA antibodies (DAKO) is performed on sections of embryonic bone according to the manufacturer's instructions.

Hypertrophy Analysis

Collagen type X—Immunohistochemistry with anti-collagen type X (quartett) is performed on sections of embryonic bone according to the manufacturer's instructions.

Animal Models:

Collagen Induced Arthritis (CIA)

CIA in mice is described in: Trentham D. E, Townes A. S, Kang A. H (1977). Autoimmunity to type II collagen: an experimental model of arthritis. J. Exp. Med. 146: 857–868.

Adjuvant-Induced Arthritis (AA)

AA is described in: Kong Y. Y et al., (1999). Activated T cells regulate bone loss and joint destruction in adjuvant arthritis through osteoprotegerin ligand. Nature, 402:304–308.

Menisectomy Model

Menisectomy is described in: Han F, Ishiguro N, Ito T, Sakai T, Iwata H. (1999). Effects of sodium hyaluronate on experimental osteoarthritis in rabbit knee joints. Nagoya J Med Sci Nov, 62(3–4):115–26

Example 1

Experimental Models for Identification of Genes Involved in the Development of Osteoarthritis and Cartilage Rehabilitation 1. Experimental Design—Model Systems In order to understand the molecular mechanisms that accompany the pathogenesis of OA, the inventors used a panel of in vitro and ex vivo models. The compilation of several complementary models facilitates the classification of several related but distinct physiological conditions according to their gene expression patterns and, subsequently, selection of genes that are critical for a specific physiological or pathological process.

The experimental strategy undertaken was based on the following preexisting knowledge:

1. Normal adult articular cartilage progenitor cells (HMSC) kept in tissue culture and freshly isolated fetal human epiphyses accurately mimic the normal pattern of gene expression of articular cartilage.

2. HMSCs treated with IGF-1 as well as the isolated human epiphyses grown in the joint simulator mimic the processes relevant to cartilage rehabilitation: normal chondrocyte maturation and excessive synthesis of high quality matrix (for HMSC) and preservation of normal cartilage architecture (for epiphyses). Note: to mimic cartilage rehabilitation following injury, a cartilage defect was made in some of the epiphyses grown in the joint simulator.

3. FGF-2 and IL-1β are both osteogenic factors that augment osteogenic initiation of HMSC.

4. Mechanical stimulation in the form of stretch or compression may cause cartilage defects that lead to degradation of the surrounding cartilage and enhanced superoxide anion and nitric oxide (NO) synthesis, thereby mimicking the OA phenotype.

Therefore, changes in gene expression caused by IGF-1 and by cartilage growth in the Joint simulator are beneficial for normal cartilage function and should be mimicked by therapeutic intervention. In contrast, changes in gene expression caused by IL1, FGF2 and mechanical stress may be connected to OA development and, therefore, should be opposed by therapeutic intervention.

1.1. In vitro Model Systems

Human Mesenchymal Stem Cells (HMSC). The pathogenesis of osteoarthritis suggests that in diseased articular cartilage, the repair processes are perturbed in the sense that mesenchymal stem cells start to differentiate not only into the chondrocyte (that is, normal) lineage but also into osteogenic and fibrogenic lineages. In addition, articular chondrocytes that are usually arrested at the stage of collagen type II differentiate further, to the stage of hypertrophic chondrocytes. This, in turn, may also augment the osteoblastic and osteoclastic (these precursors are not the resident ones and are generated within bone marrow) differentiation of progenitor cells by secretion of osteogenic factors (see above). According to pre-existing knowledge, several insults may cause the stimulation of mesenchymal stem cells and their abnormal differentiation. These include extensive changes in the composition and organization of the ECM, secretion of growth factors, cytokines, chemokines and continuous mechanical constraint. Along these lines, the identification and characterization of intracellular signaling pathways activated by different stimuli in mesenchymal stem cells represent a mandatory step. For this reason, in vitro studies were carried out in a model of adult human mesenchymal stem cell cultures, derived directly from articular cartilage. These cells were provided to the applicant by Prof. Zvi Nevo of the University of Tel Aviv School of Medicine.

The following treatments were chosen:

IGF-1: growth factor that is beneficial for normal cartilage function and rehabilitation. Inhibits the final differentiation of chondrocytes and cartilage vascularization that finally leads to its replacement by bone.

Interleukin-1: the inflammatory cytokine, known to be overproduced in OA joints. Induces expression of cartilage-degrading enzymes and bone-resorptive cytokines and bioactive molecules, like TNF-α, IL-6, soluble IL-6 receptor (sIL-6R) and NO.

FGF-2: fibroblast growth factors have been implicated in the pathogenesis of OA and animal models of this disease. Severe OA patients showed significantly higher FGF-2 concentrations than mild OA patients. Osteoclastogenesis in a co-culture system which was stimulated by the synovial fluid of severe RA patients was significantly inhibited by a neutralizing antibody against FGF-2, and this inhibition was stronger than that of antibodies against other cytokines. The inventors conclude that the increase in endogenous FGF-2 levels in the synovial fluid of OA patients may play a role in joint destruction by inducing the osteoblast (the effect that can potentially be observed directly) and osteoclast lineages (expression of some genes within target cells that may be potential indirect mediators of osteoclastic response can be observed).

Mechanical stimulation: the constant mechanical load on a joint is one of the leading causes of OA development.

1.2. Ex vivo Model Systems

Entire Isolated Epiphyses Grown in Joint Simulator*

In addition to the in vitro experiments, the inventors have also used an ex vivo model of isolated fetal human epiphyses grown in a joint simulator, which was developed by Prof. Zvi Nevo and Dr. Dror Robinson, who showed that growing isolated epiphyses in this special device causes marked proliferation of human mesenchymal stem cells, their differentiation to mature functional chondrocytes and a remarkable synthesis of high quality matrix. In contrast, epiphyses kept in regular tissue culture conditions show massive apoptosis and necrosis of the joint tissue. This model is advantageous since it better reflects genetic events that take place in the context of complex tissue (Cohen, I., Robinson, D., Cohen, N., Nevo, Z. (2000) Storing live embryonic and adult human cartilage grafts for transplantation using a joint simulating device. Biomaterials. 21:2117–2123).

*The joint simulator consists of a sterile growth chamber, fed by a closed tube system from a larger medium reservoir. Thus the cartilage positioned in the joint simulator is constantly irrigated by fresh medium enriched with $CO_2$.

Normal articular cartilage in vivo is fed by synovial fluid pumped by hydrostatic forces generated by joint movements and loading. The deeper layer of cartilage, particular of growing layers prior to the calcification of the tide mark, is fed by blood vessels. Thus, two patterns of pulsation are present in normal articular cartilage, i.e., that of joint motion and that of blood circulation. In the joint simulator, tissue is exposed to continuous flow provided at the optimal rate (defined previously) of 570 ml/h. The peristaltic pump generates pressure of a sinusoid pattern similar in range to systolic blood pressure (150 mmHg, 100 pulses/min). In summary: the advantages of the joint simulator are:

the ongoing perfusion ensures an abundant supply of nutrients and avoids accumulation of waste products;

the perfusion flow stimulates cartilage growth by mimicking hydrostatic and gravitational forces that act upon the articular cartilage.

Example 2

Establishment of Experimental Model Systems

1. In vitro Experiments

A series of in vitro experiments using HMSC was conducted. The cells were exposed to a panel of treatments which cause either chondrogenic (e.g., IGF-1) or osteogenic and angiogenic (e.g., IL1 and FGF-2) responses. Two rounds of in vitro experiments were performed. Initially, a calibration experiment was carried out in order to determine the time/dose kinetics of the cellular response to the stimuli. Based on this study, a large-scale experiment was performed from which RNA was prepared and used in the course of the gene expression profiling experiments.

1.1. Calibration of in vitro Cell System

In order to validate the differentiation response of the HMSC to the various stimuli, cells exposed to different treatments (Table 1) were tested for the expression of markers specific for osteoblastic and chondroblastic lineages by immunohistochemistry and staining procedures. To optimize the response of HMSC to differentiation treatment, it was studied on cells grown at varying density (sparse and confluent).

TABLE 1

Treatment regimes of HMSC applied in the pilot study

| Type of treatment | 0 | 1 hr | 12 hrs | 24 hrs | 48 hrs | 3 days | 6 days |
|---|---|---|---|---|---|---|---|
| No Treatment | + | | + | + | + | + | + |
| Il-1β 0.5 ng/ml and 10 ng/ml | | | + | + | + | + | + |
| IGF-1 10 ng/ml and 20 ng/ml | | | + | + | + | + | + |
| FGF-2 10 ng/ml and 100 ng/ml | | | + | + | + | + | + |
| Mechanical stress* (compression & stretching) | | + | | | | | |

*Mechanical stress - as described in experimental procedures

The following differentiation markers were tested:

Markers of Chondrocyte Terminal Differentiation and of Osteogenesis:

Osteocalcin (osteocytes);

VEGF (hypertrophic chondrocytes, angiogenesis).

Fibroblast growth factor receptor 3 (FGFR 3) (chondrocytic progenitors and upper hypertrophic chondrocytes);

Markers of Chondrogenesis:

Collagen type II (chondrocyte maturation);

Alcian Blue (chondrocyte maturation).

Figure 2:
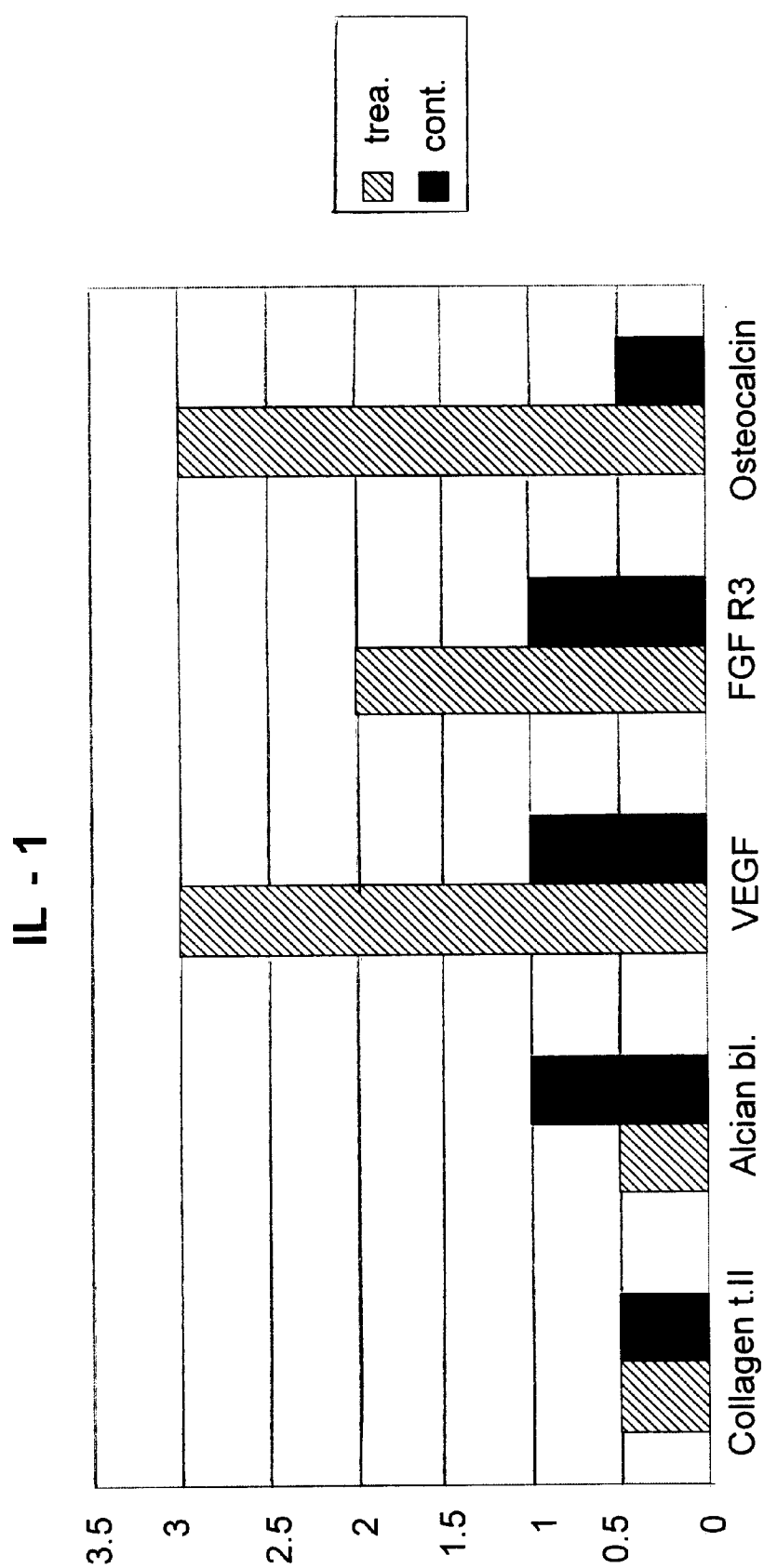
FIG. 2: Expression of various differentiation markers by confluent HMSC cells treated with IL-1β for 6 days. Control—similarly cultured non-treated cells. The level of marker expression is indicated in relative units. Abbreviations: Cont.=control; trea.=treated; Collagen t. II=Collagen type II; Alcian b1.=Alcian Blue.
Figure 3:
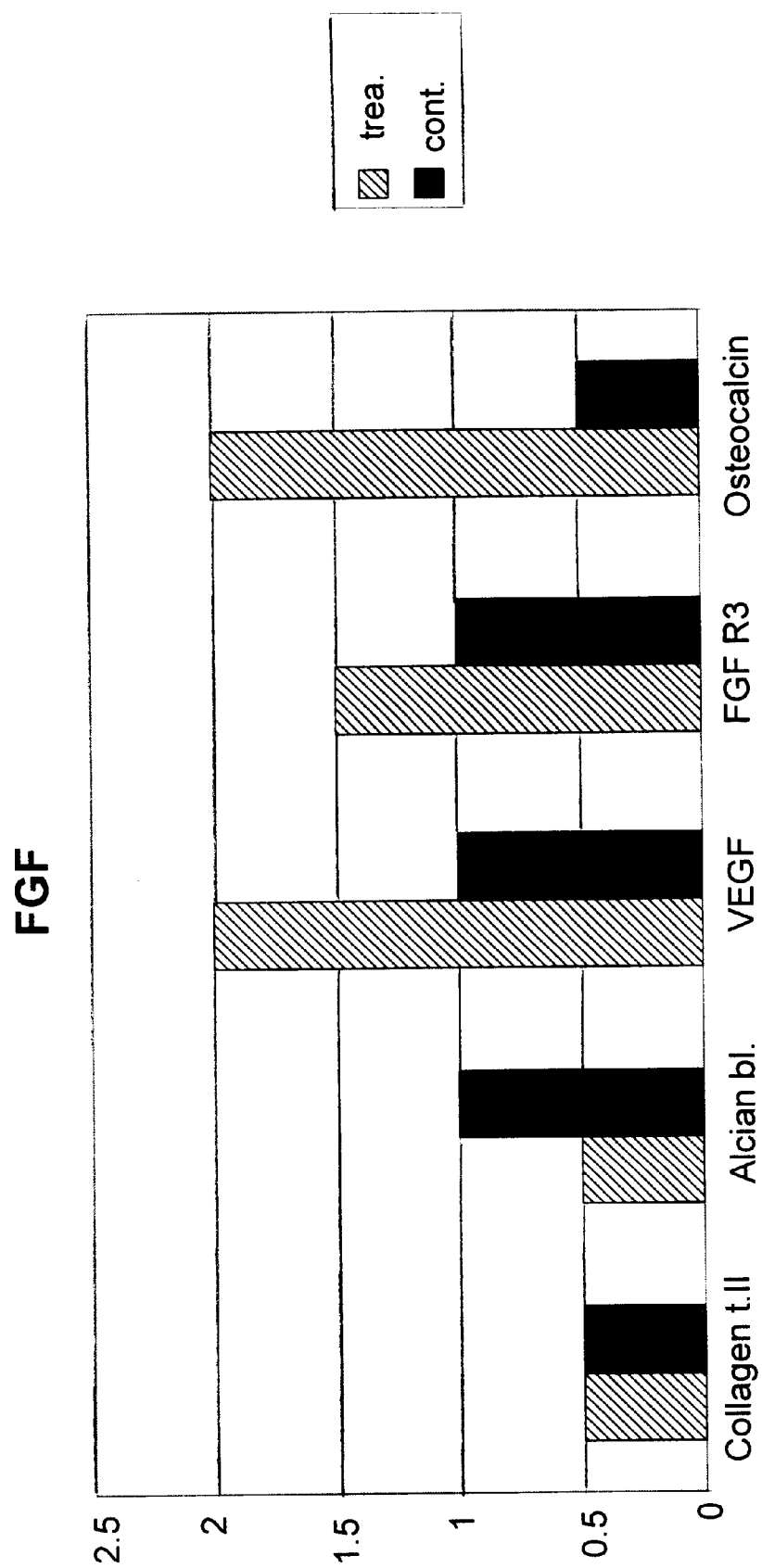
FIG. 3: Expression of various differentiation markers by confluent HMSC cells treated with FGF-2 for 6 days. Control—similarly cultured non-treated cells. The level of marker expression is indicated in relative units. Abbreviations: Cont.=control; trea.=treated; Collagen t. II=Collagen type II; Alcian b1.=Alcian Blue

The results representing the calibrated optimal treatment conditions are shown in FIGS. 1–3.

The results obtained indicate the following:

1 HMSC can grow and mature under high density (confluent) conditions displaying some signs of differentiation into both chondrogenic and osteogenic lineages, however without marked expression of markers specific for hypertrophic chondrocytes and osteocytes (see FIGS. 1–3, control cells).

2 Treatment with IGF-1 accelerates chondrocyte maturation and cartilage matrix production as demonstrated by Alcian Blue staining, by increased expression of collagen type II and decreased expression of FGFR3 (FIG. 1).

3 Treatment with either IL-1β or FGF-2 seems to have a complex effect on HMSC: the treatment
   i) induces proliferation of progenitor cells as indicated by increased FGFR-3 expression (may also reflect the induction of terminal chondrocyte differentiation, see below);
   ii) promotes terminal chondrocyte differentiation and angiogenesis as indicated by an increased VEGF expression;
   iii) stimulates osteogenesis as indicated by increased expression of osteocalcin;
   iv) inhibits normal cartilage matrix production as indicated by decreased staining with Alcian Blue.

Conclusions:
   Treatment of HMSC with IGF-1 stimulates only the chondrogenic lineage whereas the osteoblastic differentiation is somehow inhibited. Therefore, it can serve as a model system for discovery of genes whose products either promote normal chondrogenesis or inhibit the generation of osteophytes in OA.
   Treatment of HMSC with IL-1β or with FGF-2 reproduces most of the aspects of OA. Therefore, genes whose expression will be found affected by both treatments may serve as potential targets for development of anti-OA drugs.

1.2. Full Scale in vitro Experiments for Gene Expression Profiling

Based on the results of the pilot study the following adjustments were made:
   1. Only a single cytokine/growth factor dose in each treatment (instead of two doses as was originally planned) was used, since no dose dependence of HMSC response was observed. This observation can be explained by the fact that concentrations of cytokine/growth factors used in this study are above the physiological range. Thus, the maximal response could already be achieved by treatment with any of the proposed doses and their further increase did not augment the cell response. In addition, treatment with high doses of IL-1β appeared cytotoxic.
   2. The number of time points at which cells were harvested for RNA preparation was increased significantly (5 time points instead of the proposed 2) to allow for the increased resolution of development of genetic response to the treatments.

The summary of the treatment regimes used for the full-scale experiment is shown in Table 2.

TABLE 2

Treatment regimes of HMSC applied in the full-scale study

| Type of treatment | Duration of treatment | | | | | | |
|---|---|---|---|---|---|---|---|
| | 0 | 1 hr | 12 hrs | 24 hrs | 48 hrs | 3 days | 6 days |
| No Treatment | + | | + | + | + | + | + |
| IL-1β 0.5 ng/ml | | | + | + | + | + | + |
| IGF-1 10 ng/ml | | | + | + | + | + | + |
| FGF-2 10 ng/ml | | | + | + | + | + | + |
| Mechanical stress (compression) | | + | | | | | |
| Mechanical stress (tension) | | + | | | | | |

At each time point, alkaline phosphatase staining was performed. Each experiment was carried out twice, yielding 44 experiments (22 treatment regimes×2 repetitions). The RNA from these experiments was used for the preparation of the dedicated OA chip (see below) and for the generation of probes for hybridization to the "OA" chip and to the "Fibrosis" chip.

2. Ex vivo Models for OA Study

In addition to the in vitro experiments in which HMSC were employed, RNA was extracted from fetal (22 week-old) human epiphyses directly upon removal and after the 3 days growth in a joint simulator. The previously proposed 1 day time point was not analyzed since no biological effect could have been observed at this point in time. To trigger the processes of matrix rehabilitation, some of the epiphyses were injured prior to their positioning into the joint simulator. This treatment replaced the previously proposed one where the epiphyses were to be grown ex vivo under regular tissue culture conditions, as the pilot experiment demonstrated that the tissues failed to survive under such conditions. Each of the ex vivo experiments was carried out twice yielding a total of 6 experiments (i.e., 3 conditions×2 repetitions=6 experiments) (see Table 3). The RNA from the ex vivo experiments was also used for the preparation of the dedicated "OA" chip. The generated probes were hybridized to the "OA" chip and to the "Fibrosis" chip.

TABLE 3

Treatment regimes of fetal human epiphyses in the joint simulator

| Treatment | Number of epiphyses |
|---|---|
| Freshly isolated | 6 (3 per hybridization)* |
| Grown in joint simulator for 3 days | 6 (3 per hybridization) |
| Injured prior to growth in joint simulator for 3 days | 6 (3 per hybridization) |

*Each probe was prepared from RNA pools extracted from 3 similarly treated epiphyses.

Example 3

Identification of Genes Involved in the Development of Osteoarthritis and Cartilage Rehabilitation 1. Preparation of the "OA" and "Fibrosis" Chips The "OA" chip was prepared from the pool of RNA's extracted from HMSC treated as described above as well as from RNA obtained from the ex vivo experiments, by applicant's SDGI method, described in US Patent Application Publication No. WO 01/75180, fully incorporated herein by reference. It contains a total of 10,000 cDNA clones. Also the "Fibrosis" chip was prepared by applicant's said SDGI method.

2. Hybridizations to cDNA Microarrays 2.1. Probe Labeling and Hybridization to DNA Microarrays cDNA probes were synthesized from 1 μg of polyA RNA derived from every sample using reverse transcriptase (Superscript, Gibco-BRL) and 18-mer oligo-dT primer. Cy3-dCTP (Amersham) or Cy5-dCTP (Amersham) were incorporated during the RT reaction, to label the cDNA. Hybridization, subsequent scanning, and visualization were performed as previously described (Schena, M. et al. (1996) *Proc Natl Acad Sci USA* 93, 10614–10619). The quality control of hybridizations was performed according to applicant's methods.

2.2. The Hybridization Scheme cDNA probes were hybridized to the OA and to the Fibrosis human cDNA microarrays according to the scheme presented in Table 3.

Probe 2 in all hybridizations was an identical probe comprised of a pool of 0 time point RNA extractions (Table 4, Common control). This served as a common normalizing probe and allowed us to compare results from different hybridizations in formal statistical analysis. Probe 1 in each hybridization was prepared from RNA extracted from cells or ex vivo organ cultures cultivated under the defined treatment conditions. The entire hybridization set was repeated twice, yielding a total of: 26 hybridizations types X 2 cDNA microarrays X 2 repetitions=104 hybridizations.

TABLE 4

Hybridization scheme

| Probe No. | Probe Name | Dye | Human articular cartilage RNA, Treatment. |
|---|---|---|---|
| 1 | SOA1 | cy5 | Control 12 h |
|  | NML21 (Common ctrl') | cy3 | Normal |
| 2 | SOA2 | cy5 | Control 24 h |
|  | NML21 (Common ctrl') | cy3 | Normal |
| 3 | SOA3 | cy5 | Control 48 h |
|  | NML21 (Common ctrl') | cy3 | Normal |
| 4 | SOA4 | cy5 | Control 3 days |
|  | NML21 (Common ctrl') | cy3 | Normal |
| 5 | SOA5* | cy5 | Control 6 days |
|  | NML21 (Common ctrl') | cy3 | Normal |
| 6 | SOA6 | cy5 | IL-1b 12 h |
|  | NML21 (Common ctrl') | cy3 | Normal |
| 7 | SOA7 | cy5 | IL-1b 24 h |
|  | NML21 (Common ctrl') | cy3 | Normal |
| 8 | SOA8 | cy5 | IL-1b 48 h |
|  | NML21 (Common ctrl') | cy3 | Normal |
| 9 | SOA9 | cy5 | IL-1b 3 days |
|  | NML21 (Common ctrl') | cy3 | Normal |
| 10 | SOA10 | cy5 | IL-1b 6 days |
|  | NML21 (Common ctrl') | cy3 | Normal |
| 11 | SOA11 | cy5 | IGF-1 12 h |
|  | NML21 (Common ctrl') | cy3 | Normal |
| 12 | SOA12 | cy5 | IGF-1 24 h |
|  | NML21 (Common ctrl') | cy3 | Normal |
| 13 | SOA13 | cy5 | IGF-1 48 h |
|  | NML21 (Common ctrl') | cy3 | Normal |
| 14 | SOA14 | cy5 | IGF-1 3 days |
|  | NML21 (Common ctrl') | cy3 | Normal |
| 15 | SOA15 | cy5 | IGF-1 6 days |
|  | NML21 (Common ctrl') | cy3 | Normal |
| 16 | SOA16 | cy5 | FGF-2 12 h |
|  | NML21 (Common ctrl') | cy3 | Normal |
| 17 | SOA17 | cy5 | FGF-2 24 h |
|  | NML21 (Common ctrl') | cy3 | Normal |
| 18 | SOA18 | cy5 | FGF-2 48 h |
|  | NML21 (Common ctrl') | cy3 | Normal |
| 19 | SOA19 | cy5 | FGF-2 3 days |
|  | NML21 (Common ctrl') | cy3 | Normal |
| 20 | SOA20 | cy5 | FGF-2 6 days |
|  | NML21 (Common ctrl') | cy3 | Normal |
| 21 | OA23 | cy5 | Joint simulator with injury 3 days |
|  | NML21 (Common ctrl') | cy3 | Normal |
| 22 | OA24 | cy5 | Joint simulator 3 days control |
|  | NML21 (Common ctrl') | cy3 | Normal |
| 23 | OA27 | cy5 | Freshly isolated epiphyses |
|  | NML21 (Common ctrl') | cy3 | Normal |
| 24 | SOA30 | cy5 | HMSC |
|  | NML21 (Common ctrl') | cy3 | Normal |
| 25 | SOA31 | cy5 | 17 weeks AC 1 hr compression (MF) |
|  | NML21 (Common ctrl') | cy3 | Normal |
| 26 | SOA32 | cy5 | 17 weeks AC 1 h tension (MF) |
|  | NML21 (Common ctrl') | cy3 | Normal |

*Probe SOA5 has displayed artifactual behavior and was therefore removed from further analysis.

2.3. Analysis of Hybridization Results

The hybridization data were analyzed using an algorithm for quality control and two different algorithms for gene clustering.

2.3.1 Quality Control

Quality control is aimed at achieving a correct balancing of the Cy3 and Cy5 signals, to detect "suspicious" signals that putatively have poor differentials at a given hybridization and to transform the raw data into the appropriate form for subsequent analysis. The algorithm of detection of "suspicious" pixels that have putatively poor differentials for a given hybridization is based on the stability of two-dimensional distributions of logarithms of common control signals obtained from different hybridizations of one experimental set. Normally, this distribution is concentrated along a diagonal and has a reasonable stability of variance. According to this variance a score of a pixel to be "suspicious" is calculated and such pixels are automatically marked. In the case that only a part of the pixels is "suspicious" the hybridization proceeds to further analysis; however, it is known which data are reliable and which are not.

2.3.2 Clustering Algorithms

Algorithm 1. This procedure is "blind" and does not require the a prion knowledge of inter-relationships between the biological conditions. Clusterization is based on the identification of the densest areas within the multidimensional space where the analyzed genes are points in this space. The density is measured by either correlation or Euclidian distance. The procedure is roughly as follows. The area in space that is mostly rich with the analyzed genes is chosen; this set is regarded as the $1^{st}$ cluster. The $2^{nd}$ cluster is the next densest area that does not intersect with the first one and so on. The radius of the area is defined according to the principle that the average appearance of the randomized genes in the area is 1. These narrow clusters can be further combined in the more wide ones according to their proximity in space. The identified clusters are ranked according to the degree of their contribution to the covariation matrix of the total gene expression profiles.

Algorithm 2. When the biological classification of different hybridizations within the analyzed set can be hypothesized, genes whose behavior strongly correlates with this hypothesis can be detected. For every gene, Fisher criterion of the significance of its discriminative behavior is calculated. The most significant genes are the discriminative ones.

The analysis of results was performed according to the following scheme:

1. Quality control—separately for each microarray.
2. Clustering by algorithm 1—separately for each microarray.
3. Clustering by algorithm 2—separately for each microarray.
4. Comparison of clustering data—separately for each microarray.
5. Generation of a unified clustered gene expression data set that contains genes selected only by algorithm 1, only by algorithm 2 and by both—separately for each microarray.
6. Identification of the most prominent gene expression patterns (clusters) and selection of genes for sequencing and annotation according to them.
7. Sequence-based (after contigization by said algorithm) comparison of sets of genes selected from both microarrays and verification that expression patterns of identical genes are identical.
8. Generation of a non-redundant list of clustered genes obtained from both microarrays.
9. Advanced annotation of non-annotated clones that have identity to EST's (contigization and homology search).
10. Advanced annotation of unknown genes and putative proteins (homology search and domain analysis).

11. Literature analysis of known genes.
2.4. Results

After performing the full analysis of hybridization results the inventors ended up with a list of genes, from which 57 genes were derived from the "Fibrosis" chip and 197 genes were derived from the "OA" chip. Some of the known genes were analyzed in the light of information available from biomedical literature and from public databases.

IL-1 and FGF-regulated genes were of major interest because of their potential implication in the osteoarthritic phenotype (see above), i.e., degradation of cartilage matrix and stimulation of ectopic bone formation.

Therefore, genes whose expression was influenced by treatment with FGF-2, were of particular interest for the purpose of the present invention.

The genes that fall in this category are those, the expression of which changed in FGF-treated cells compared to the non-treated biological control.

One of the identified genes that were up-regulated by bFGF-2, with unknown involvement in arthritic diseases has been found to be spermidine synthase (also denoted as SEQ ID No. 1).

Spermidine is one of the three bioactive polyamines. In epiphyseal cartilage from calf scapulas, they are more concentrated in the ossifying area, where calcification takes place, than in the resting region. Spermidine is present in greater amounts than spermine and putrescine. Since ornithine decarboxylase is measurable only in the resting region of the tissue, it is in this area that polyamine biosynthesis occurs, while they accumulate in the ossifying area. Immunohistochemical evidence is obtained that spermidine is extracellular only in the ossifying zone. Therefore, polyamines may be related to calcification of preosseous cartilage (Vittur F., et al. 1986). Spermidine-dependent proteins were shown to be involved in the fusion of mouse alveolar macrophages induced by 1α,25-dihydroxyvitamin D3. and interleukin 4. Polyamines, most likely spermidine, are involved as an important intracellular mediator of the 1α,25-dihydroxyvitamin D3 action in inducing protein synthesis, which in turn induces fusion of macrophages. When spermidine synthesis was inhibited by adding methylglyoxal bis(guanylhydrazone) (MGBG), the enhanced synthesis in 9 of the 14 proteins induced by 1α,25(OH)$_2$D3 was greatly diminished with a concomitant inhibition of fusion. Further addition of spermidine restored the synthesis of these 9 proteins and the fusion as well. Since osteoclasts, for their activation, must also undergo the fusion process, polyamines may play some role in osteoclast activation as well. This hypothesis is supported also by the known role vitamin D in the development of the skeleton. (Hayashi T., et al., 1986)

Here for the first time the inventors demonstrate up-regulation of spermidine synthase by treatment of HMSC cells with FGF-2 that may have an osteogenic effect. Therefore, spermidine synthase is a preferred target for screening candidate drugs for the treatment of OA.

Example 4

Evaluation of Spermidine Synthase Inhibitors as Potential Drugs for OA

Selection of spermidine synthase as a target for screening candidate inhibitors as potential drugs for inhibiting or delaying OA was based on its up-regulation upon bFGF-2 treatment (3 ng/ml bFGF, 50 mg/ml ascorbic acid and $10^{-8}$ M dexamethasone) as disclosed herein. Furthermore, in situ hybridization studies performed on human embryonic bone showed expression of spermidine synthase in synovial membrane, in osteogenic cells on osteoblasts surrounding the trabecula, and in endostium. A signal was also observed in chondrocytes of developing bone.

The potential involvement of spermidine synthase in OA was supported by the following findings:

1. Ossifying cartilage contains more polyamines than the resting zone. The amount of spermidine in the ossifying zone is 5-fold higher, and that of spermine about double. The spermidine/spermine ratio is 1.7 in the ossifying cartilage and 0.69 in the resting zone. (Vittur F., et al. 1986).
2. Elevated levels of polyamines were detected in synovial fluid from arthritis patients. (Nesher G., et al. , 1997)
3. ODC biosynthesis inhibitor prevents the development of collagen-induced arthritis (CIA), as well as causing decreased spermidine levels and serum anti-CII antibody levels. (Wolos J. A., et al. , 1990)
4. Inhibition of spermidine synthesis inhibits macrophage fusion. Addition of spermidine restores the activity. (Hayashi T., et al., 1986)
5. In vitro studies show that, of the three polyamines, only spermidine has the ability to displace proteoglycan subunits from a column of type II collagen. (Vittur F., et al. 1986).
6. Alkaline phosphatase activity (a marker of hypertrophy and calcification) is enhanced by spermidine. (Vittur F., et al. 1986).

Figures 4A, 4B:
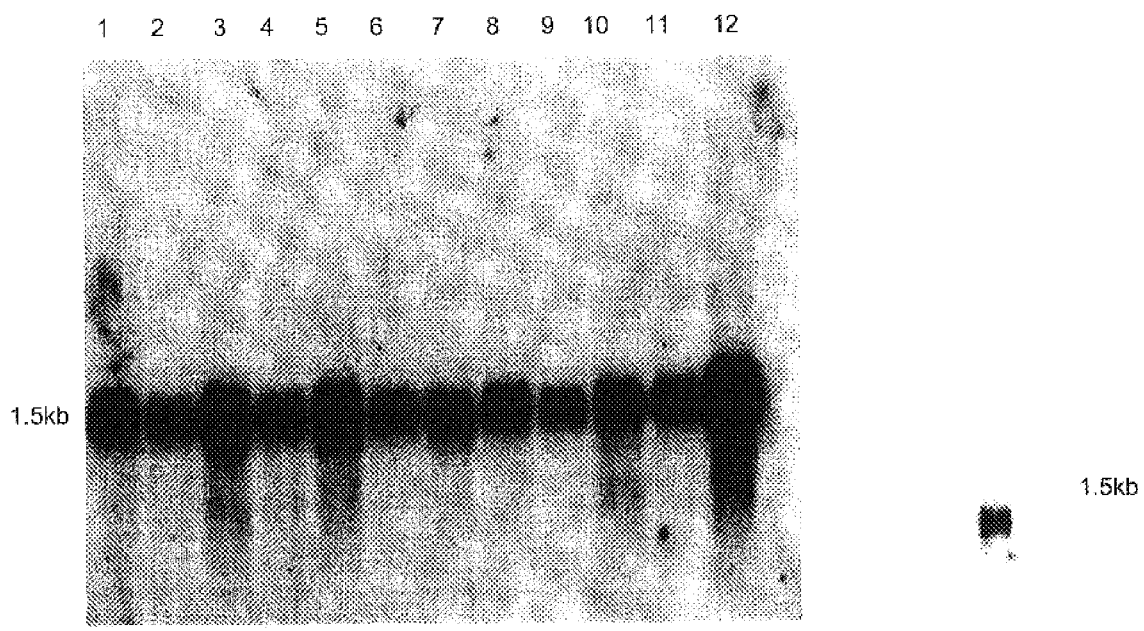
FIGS. 4A–4B: Northern blot analysis of spermidine synthase. 4A: shows tissue Northern blot analysis of spermidine synthase: lane 1: brain; lane 2-colon; lane 3-heart; lane 4-kidney; lane 5-liver; lane 6-muscle; lane 7-lung; lane 8-placenta; lane 9-small intestine; lane 10-spleen; lane 11-stomach; lane 12-testis. 4B: Northern blot analysis of spermidine synthase in U2OS osteoblastic cells.

As a first general analysis, the expression pattern of spermidine synthase in different tissues was examined by Northern blot analysis. As shown in FIG. 4, the expected 1.3 Kb mRNA was detected in all tissues examined.

1. Potential Spermidine Synthase Inhibitors

Evaluation of different spermidine synthase inhibitors as candidate drugs for the treatment of OA is performed using the following available known spermidine synthase inhibitors:

adenosyl spermidine

AdoDATO

DCHA trans-4-Methylcyclohexilamine (4MCHA)

Cyclohexylamine

Methylglyoxal his (cyclopentylamidinohydrazone) (MGBP)

2-mercaptopropylamine

N-chlorosulfonyldlcyclohexylamme

5'-((3-aminopropyl) amino)-5'-deoxyadenosine

1-Aminooxyl-3-aminopropane

5'-(isobutylthio) adenosine

5'-(Methylthio) adenosine

Further evaluation analyses are performed using new spermidine synthase inhibitors that are obtained by the following screening methods:

1.1. Radioactivity-Based Assay:

Radioactive enzymatic assays for spermidine synthase were described in Raina. A., Eloranta, T., Pajula, R. L. (1983). Rapid assay for putrescine aminopropyltransferase (spermidine synthase) and spermidine aminopropyltransferase (spermine synthase). Methods in Enzymology, 94:257–260.). These assays involve the use of $^3$H-, $^{14}$C-, or $^{35}$S-labled S-adenosylmethionine (SAM) (prepared from labled methionine using SAM synthetase from *E. coli*). The choice of the initial atom to be labeled in methionine determines which of the products, spermidine or methyladenosine (MTA), becomes labeled. Initially, the assay protocol involved the use DL-(2-$^4$C) methionine, which results in the labeled product being spermidine. This protocol results in tedious separation of the labeled spermidine from labeled reactant-decarboxylated SAM, a protocol that is not compatible with high throughput screening (HTS). A modification of this assay, which involves the use of L-(methyl-$^{14}$C) methionine, leads to the labeling of the other product, methyladenosine, which greatly simplifies the assay to the extent that it is now a candidate for HTS-compatible bioassay development. Briefly, the assay involves the separation of labeled decarboxylated SAM from MTA. This is achieved by the use of a phosphocellulose cation exchanger which, under acidic conditions, binds MTA, but not decarboxylated SAM.

1.2. Fluorescence-Based Assay:

Different fluorescence-based assays have been developed for the identification of primary and secondary amines. In this assay primary amines are protected first by reaction with salicylaldehyde to give a Schiff base. Since spermidine and putrescine differ by the former having a secondary amine, this amine is reacted with dansyl chloride or NBD chloride to produce a fluorescent product.

2. Evaluation of Spermidine Synthase Inhibitors as Potential Drugs for OA

In order to evaluate the applicability of different spermidine synthase inhibitors as potential drugs for OA, the different inhibitors were examined for their ability to lead to inhibition or attenuation of chondrocyte proliferation and terminal differentiation, as well as to inhibition of development of arthritis. The different inhibitors were examined using the following evaluating test systems:

2.1. In vitro Test System 2.1.1. Subcloning of the Human Spermidine Synthase Full-Length cDNA The entire ORF of human spermidine synthase (accession numbers—BC000309 and NM_003132) was cloned by RT-PCR using RNA extract from U2OS cells. The RT-PCR product was double-digested with AvrII and KpnI and subcloned into the pCMVNSV-neo and into pBScKS for TNT reaction. In addition, the full ORF with a His-Tag at the N-terminus was also cloned by RT-PCR. The RT-PCR product was digested with AvrII and subcloned into pBSc for TNT reaction. This construct was digested with NotI and HindIII and the insert was subcloned into pCMVNSV-neo NotI-HindIII. All four constructs were fully sequenced, and the sequence analysis demonstrated a complete match of the cloned sequence with the published sequence. An additional expression vector was prepared by subcloning this gene into the pIRES-puro expression vector (Clontech).

Figure 5:
FIG. 5: Western blot analysis of 293 cells transiently transfected with spermidine synthase. Western blots were probed with anti-His antibodies. Lane 3: lysates of transfected cells; Lane 4: medium of transfected cells; Lane 5: lysates of 293 control cells; Lane 6: medium of 293 control cells; Lane7: positive control.

2.1.2. Examination of Spermidine Synthase Constructs by Transient Transfection of 293 Cells In order to examine the constructs, transient transfection of 293 cells with the human spermidine synthase cDNA (containing His-tag and cloned into pIRES puro) was performed. Cells were grown in serum-free medium for two days and the media and lysates were collected. Proteins were separated on 10% SDS gel followed by blotting. Membrane was reacted with anti-His antibodies. The expected band of 35 kDa (representing one subunit of spermidine synthase) was observed (FIG. 5).

2.1.3. Enhanced Proliferation or Differentiation Rate in Transfected Cells

Different end point parameters indicating inhibition of chondrocyte proliferation and terminal differentiation by a test spermidine synthase inhibitor are examined using various transfected cell lines (e.g., chondrocytes, endothelial cells) over-expressing exogenous human spermidine synthase gene. Higher proliferation or differentiation rate indicates that the said gene is possibly involved in pathways that induce arthritis.

2.1.4. Establishment of Stable Transfected Cell Line

Figure 6:
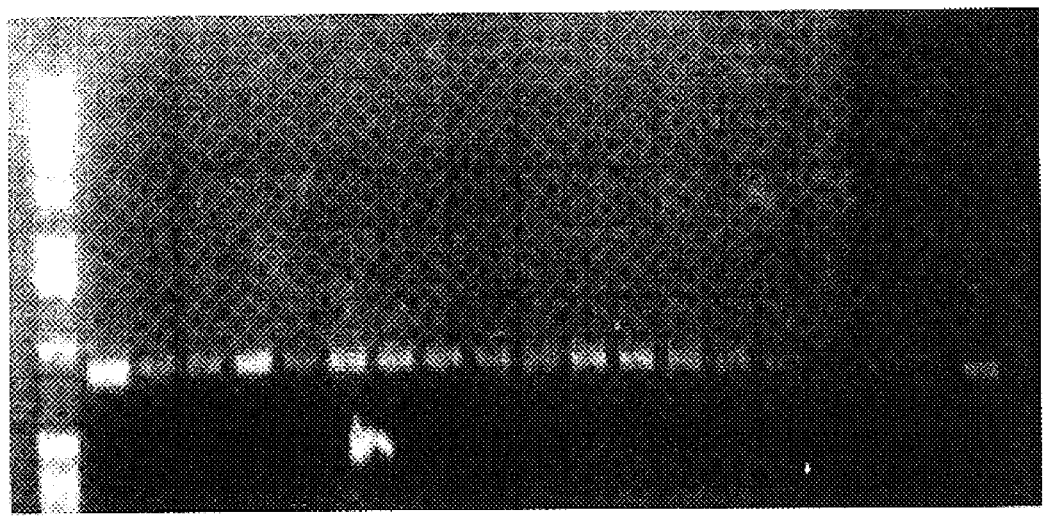
FIG. 6: PCR analysis of RCJ3.1C5.18 cells stably transfected with spermidine synthase. Numbers represent different clones.

The human spermidine synthase cDNA lacking the His-Tag, cloned into the pCMVneo expression vector, was used for stable transfection of the RCJ3.1.C5.18 cell line. More than 30 clones were isolated and screened using RT-PCT (presented in FIG. 6). The highest expressing clones were selected for drug evaluating experiments.

The effect of spermidine synthase over-expression was examined using different end point parameters indicating chondrocyte proliferation, chondrocyte final differentiation, angiogenesis and osteoclastogenesis. These parameters have been previously shown to be related to OA. The in vitro test system of the invention is used as well for evaluation of the ability of different spermidine synthase inhibitors to inhibit and attenuate these effects.

Differentiation of chondrocytes is evaluated by Alcian Blue staining (stains cartilage proteoglycans), alkaline phosphatase activity and collagen type X immunohistochemical staining. Increase in alkaline phosphatase activity or in collagen type X immunohistochemical staining indicates final differentiation of chondrocytes.

Proliferation of chondrocytes is evaluated by measuring cell number and thymidine incorporation.

2.2. Ex vivo Test System

The effect of spermidine synthase inhibition on cartilage and bone formation by different candidate inhibitors is examined ex vivo using embryonic bone organ culture expressing endogenous spermidine synthase. Hind legs are obtained from mouse embryo (E16). Bone cultures are performed in—modified Eagle's medium supplemented with 10% fetal calf serum (FCS), 0.05 mg/ml ascorbic acid, and 1 mM -glycerolphosphate. One bone per well is cultured in 300 1 complete medium in a 24-well tissue culture plate, in a 5% $CO_2$, incubator at 37° C. and 98% humidity. Increasing concentrations of different spermidine synthase inhibitors such as the AdoDATO inhibitor-(5 –50 M) are added to the culture medium and bones are cultured for 7 days. Bones treated with the candidate inhibitor, as well as control bones, are evaluated at time 0 and after 7 days of culture.

Sections prepared from control and treated bones are stained using alizarin red (stains calcified tissues) and Alcian Blue (stains cartilage proteoglycans) for evaluating chondrocyte final differentiation. Longitudinal growth of the bone is calculated as the increase in length of the hypertrophic region and the calcified bone. Hypertrophy is further evaluated using typeX collagen staining. Proliferation is examined by PCNA.

2.3. In vivo Test System

The effect of different spermidine synthase inhibitors on different parameters related to OA such as chondrocyte proliferation, terminal differentiation and development of arthritis, is evaluated using two in vivo systems; one system over-expresses exogenous spermidine synthase and the other expresses endogenous spermidine synthase. Both test systems are used by the present invention as a model for OA.

2.3.1. Transgenic Mice Expressing Exogenous Spermidine Synthase

The effect of spermidine synthase over-expression is examined using different end point parameters indicating chondrocyte proliferation, chondrocyte final differentiation, angiogenesis and osteoclastogenesis, and development of arthritis.

Transgenic FVBN mice expressing human spermidine synthase cDNA under collagen type II promoter/enhancer have been established. Cartilage development is examined in sections obtained from transgenic mouse embryos (E17) or from 1-week-old mice. Evaluation of final differentiation is performed by staining of sections with Alcian Blue and alizarin red. Evaluation of proliferation is performed by PCNA.

The development of arthritis is examined in adult spermidine synthase transgenic mice by examining paw thickness. In order to facilitate spermidine synthesis in these transgenic animals, mice are treated with decarboxylated SAM (a substrate of spermidine synthase). Decarboxylated SAM is dissolved in drinking water and administered orally.

2.3.2. Arthritic Rats Expressing Endogenous Spermidine Synthase

As an in vivo evaluating system expressing endogenous spermidine synthase, the arthritic rat model is used. Collagen arthritis is induced in Female Lewis rats according to the method of Trentham (Trentham D. E, Townes A. S, Kang A. H (1977). Autoimmunity to type II collagen: an experimental model of arthritis. J. Exp. Med. 146: 857–868). The emulsion was prepared by adding 1.6 mg/ml of bovine collagen type II and 0.4 mg/ml of adjuvant peptide solution to an equal volume of Freund's incomplete adjuvant (DIFCO, Mich.) and stirring with an homogenizer for 15 minutes, 4° C. at 10,000 rpm. On day 0, each animal receives 0.8 mg of collagen in 1 ml emulsion intradermally.

The effect of spermidine synthase inhibition by different candidate inhibitors is evaluated in this system using different end point parameters indicating chondrocyte proliferation, chondrocyte final differentiation, angiogenesis and osteoclastogenesis, and development of arthritis.

Different spermidine synthase inhibitors can be administered to arthritic rats (collagen type II induced arthritis (CIA)). The inhibitors are dissolved in water and administered orally or directly into the joint of the arthritic rats. The development of arthritis is monitored by measuring paw thickness. In addition, histological examination is performed on sections obtained from treated and control animals.

Evaluation of final differentiation is performed by staining of sections with Alcian Blue and alizarin red. Evaluation of proliferation is performed by PCNA.

REFERENCES

Vittur F., Lunazzi G., Moro L., Stagni N., de Bernard B., Moretti M., Stanta G., Bacciottini F., Orlandini G., Reali N. et al. A possible role for polyamines in cartilage in the mechanism of calcification. Biochem Biophys Acta 1986 March 19; 881 (1): 38–45.

Hayashi T., Shinki T., Tanaka H., Abe E., Suda T. Polyamines are involved in the 1-alpha,25 dihydroxyvitamin D3-induced fusion of mouse alveolar macrophages. J Bone Miner Res. 1986. April 1(2):235–42.

Nesher G., Osborn T G., Moore T L. Effect of treatment with methotrexate, hydroxychloroquine, and prednisone on lymphocyte polyamine levels in RA: correlation with the clinical response and rhematoid factor synthesis. Clin Exp Rheumatol 1997. July-August; 15(4):343–7.

Wolos J A, Logan D E, Bowlin T L. MAP, an inhibitor of polyamine biosynthesis, prevents the development of collagen-induced arthritis. Cell Immunol 1990 February; 125(2):498–507.

What is claimed is:

1. A method for the treatment of a subject in need of treatment for osteoarthritis comprising administering to said subject an amount of an inhibitor of spermidine biosynthesis sufficient to effect a substantial inhibition of spermidine biosynthesis so as to thereby treat the subject.

2. The method according to claim 1, wherein said inhibitor is a spermidine synthase inhibitor.

3. The method of claim 2 wherein said spermidine synthase inhibitor is selected from the group consisting of adenosyl spermidine, AdoDATO, CHA, trans-4-methylcyclohexylamine (4MCHA), cyclohexylamine methylglyoxal bis (cyclopentylamidinohydrazone) (MGBP), 2-mercaptopropylamine, N-chlorosulfonyldicyclohexylamine, 5'-((3-aminopropyl)amino)-5'-deoxyadenosine, 1-aminooxyl-3-aminopropane, 5'-(isobutylthio) adenosine, 5'-(methylthio) adenosine.

* * * * *